US011627740B2

(12) United States Patent
Castagnaro et al.

(10) Patent No.: US 11,627,740 B2
(45) Date of Patent: Apr. 18, 2023

(54) GLYCOSIDE COMPOUND OF FATTY ACIDS, COMPOSITION COMPRISING IT, PROCESS FOR ITS OBTENTION AND METHODS TO APPLY IT ON PLANTS OR FRUITS OR BOTH AT THE SAME TIME

(71) Applicants: Consejo Nacional de Investigaciones Científicas y Técnicas (Conicet), Ciudad Autónoma de Buenos Aires (AR); ESTACION EXPERIMENTAL AGROINDUSTRIAL OBISPO COLOMBRES, Tucuman (AR); Bjorn Gunnar Viking Welin, Alicante (ES)

(72) Inventors: Atilio Pedro Castagnaro, Tucuman (AR); Maria Paula Filippone, Tucuman (AR); Bjorn Gunnar Viking Welin, Alicante (ES); Carlos Froilan Grellet Bournonville, Tucuman (AR); Alicia Ines de Fatima Mamaní, Tucuman (AR); Pía de los Angeles Di Peto, Tucuman (AR)

(73) Assignees: Consejo Nacional de Investigaciones Científicas y Técnicas (CONICET), Buenos Aires (AR); ESTACION EXPERIMENTAL AGROINDUSTRIAL OBISPO COLOMBRES, Tucuman (AR)

( * ) Notice: Subject to any disclaimer, the term of this patent is extended or adjusted under 35 U.S.C. 154(b) by 339 days.

(21) Appl. No.: 16/644,614

(22) PCT Filed: Sep. 5, 2018

(86) PCT No.: PCT/IB2018/056778
§ 371 (c)(1),
(2) Date: Mar. 5, 2020

(87) PCT Pub. No.: WO2019/049044
PCT Pub. Date: Mar. 14, 2019

(65) Prior Publication Data
US 2021/0059250 A1    Mar. 4, 2021

Related U.S. Application Data

(60) Provisional application No. 62/554,677, filed on Sep. 6, 2017.

(51) Int. Cl.
*A01N 43/16* (2006.01)
*C07H 13/06* (2006.01)
*C07H 1/08* (2006.01)

(52) U.S. Cl.
CPC ............... *A01N 43/16* (2013.01); *C07H 1/08* (2013.01); *C07H 13/06* (2013.01)

(58) Field of Classification Search
CPC ................................. C07H 13/06; A01N 43/16
See application file for complete search history.

(56) References Cited

U.S. PATENT DOCUMENTS

2011/0100079 A1* 5/2011 Kamei ..................... A01G 7/06
71/11

FOREIGN PATENT DOCUMENTS

WO    WO2014145380    9/2014

OTHER PUBLICATIONS

Ibrahim et al., Int. J. Exp. Path., 2015, 96, p. 87-93. (Year: 2015).*
Bournonville et al., Scientific Reports, 2020, 10, 8196, 12 pages. (Year: 2020).*
Bournonville et al., Scientific Reports, 2020, 10:8196, 12 pgs. (Year: 2020).*
Neri et al., Agronomy, 2021, 11, 1643, 11pgs. (Year: 2021).*
Ibrahim et al., International Journal of Experimental Pathology, 2015, 96, p. 87-93. (Year: 2015).*
Kim et al. "Characterisitcs of sophorolipid as an antimicrobial agent", Journal of Microbiology and Biotechnology, Korean Society for Applied Microbiology, Seoul, KR vol. 12, No. 2, Jan. 1, 2002, pp. 235-241.

* cited by examiner

*Primary Examiner* — Jonathan S Lau
(74) *Attorney, Agent, or Firm* — Defillo & Associates, Inc.; Evelyn A. Defillo

(57) ABSTRACT

A glycoside compound of fatty acids that includes the general formula: GalNAc-GalNAc-Glc-O—R, where GalNAc is α- or β-D-N-acetylgalactosamine, Glc-O—R is a molecule of α- or β-D-glucose esterified to a monounsaturated fatty acid (R), where R is selected from 12:1(n) and where n is an integer between 2 and 11; 11:1(n) and where n is an integer between 2 and 10; 10:1(n), and where n is an integer between 2 and 9; 9:1(n), and where n is an integer between 2 and 8; 8:1(n), and where n is an integer between 2 and 8; 7:1(n) and where n is an integer between 2 and 7; and 6:1(n), and where n is an integer between 2 and 6. The compound has activity against plant pathogens, and induces the defense, and promotes the growth, of plants.

4 Claims, 12 Drawing Sheets
Specification includes a Sequence Listing.

GLYCOSIDE COMPOUND OF FATTY ACIDS, COMPOSITION COMPRISING IT, PROCESS FOR ITS OBTENTION AND METHODS TO APPLY IT ON PLANTS OR FRUITS OR BOTH AT THE SAME TIME

CROSS REFERENCE TO RELATED APPLICATION

This application is a national stage entry of PCT/162018/056778 filed Sep. 5, 2018, under the International Convention claiming priority over U.S. provisional application No. 62/554,677 filed Sep. 6, 2017.

FIELD OF THE ART

The present invention relates to a glycoside compound of fatty acids, to a composition comprising it, to a process for its obtention and to methods for its application to plants or fruits or both at the same time, where said glycoside compound of fatty acids has a general formula: GalNAc-GalNAc-Glc-O—R, where GalNAc is α- or β-D-N-acetyl-galactosamine, Glc-O—R is a molecule of α- or β-D-glucose esterified to a monounsaturated fatty acid (R), where R is selected from 12:1(n) and where n is an integer between 2 and 11; 11:1(n) and where n is an integer between 2 and 10; 10:1(n), and where n is an integer between 2 and 9; 9:1(n), and where n is an integer between 2 and 8; 8:1(n), and where n is an integer between 2 and 8; 7:1(n) and where n is an integer between 2 and 7; and 6:1(n), and where n is an integer between 2 and 6. The compound has activity against plant pathogens, and induces plant defense and promotes plant growth.

BACKGROUND OF THE INVENTION

Plant diseases caused by bacteria are very difficult to control and in the agricultural production there are very few products available to treat bacterial diseases. One of the few commercial alternatives for handling bacterial infections is copper, which has been used in agriculture for several centuries as a treatment for leaves, to protect plants against fungal and bacterial diseases. However, when systematically used at a bactericidal level, copper is toxic and consequently it is not deemed to be an effective treatment, or an advisable one, in a large scale.

The second type of bactericides found to provide a control of bacterial diseases is antibiotics. The two main ones tagged for their use in agriculture are streptomycin sulfate and oxytetracycline. These products have been in use on plants since the 1950's, but they are also important in human and animal medicine and consequently only a fraction of one percent of the whole domestic use of these antibiotics is for agriculture (www.nass.usda.gov, United States Government Accountability Office (2011)). Streptomycin is the preferred bactericide, because it kills bacteria by contact (bactericide), while oxytetracycline is bacteriostatic and suppresses bacterial growth. Bacteriostatic bactericides require a longer period of exposition to sufficiently suppress growth so as to reduce the bacterial titer.

In every kind of agriculture, plant pathogen fungi cause devastating losses ranging into millions of dollars in diverse crops all over the world. Therefore, the extensive application of synthetic fungicides has been used to control plant pathogen fungi, but the repeated use of these fungicides for decades has altered natural biological systems and, on occasions, it has resulted in the development of resistance in fungi. Besides, many of these pesticide products have had undesirable effects on organisms that were not the targets and have fostered environmental and human health concerns Therefore, taking into consideration what has been said above, the search for crop protection alternatives that are friendlier to the environment and health has been of maximum priority to develop a more sustainable agricultural production. One of the most promising strategies is the triggers of plant immunity, elicitors, inducers or biocontrollers, that are formulated on the basis of substances (molecules) of natural origin (microbial or vegetal) that make plants increase the level of their own defenses against the pathogenic organisms that harm them.

Generally speaking, it is known that these defense inducer molecules commence a signaling process in a plant that leads to the activation of a series of biochemical responses that prevent or delay the advance of pathogenic microorganisms (Bonas and Lahaye, Curr. Opin. Microbiol. (2002) 5:44-50).

Among the advantages of bioproducts or inducer bioinputs it can be listed that they are biodegradable, have a wide spectrum of action against fungi and bacteria, have a low resistance-generating potential, scarce toxicity for human beings and, besides, usually a low production cost (NUrnberger and Brunner, Curr. Opin. Plant Biol. (2002) 5:318-24).

Some glycolipids of fungal origin are known to have antimicrobial activity, for example in the article Microbiological Research 168 (2013) 22-32. Also known are sophorolipids with antimcrobial activity (J. Microbiol. Biotechnol. (2002), 12(2), 235-241) and a glycolipid isolated from a fungus, that exhibits antimicrobial activity (African Journal of Microbiology Research Vol. 5(17), pp. 2512-2523, 9 September, 2011). Glycolipids of trehalose, that act upon the hydric stress of plants (CN105831159) and glycolipids such as the lipid of mannosyl erythritol (MEL) and lipid of mannosyl mannitol (MML) of yeasts for the control of natural yeasts (JP2010215593) have also been disclosed. Also known are fatty acid esters; fatty acid esters of sugars alcohols, and alkyl glycosides that impart tolerance to stress, to plants (US 2011/0100079).

BRIEF DESCRIPTION OF THE PRESENT INVENTION

Definition: The Term FL or FLs is the Compound According to the Present Invention It is provided a glycoside compound of fatty acids that comprises the general formula GalNAc-GalNAc-Glc-O—R, where GalNAc is α- or β-D-N-acetylgalactosamine, Glc-O—R is a molecule of α- or β-D-glucose esterified to a monounsaturated fatty acid (R), where R is selected from 12:1(n) and where n is an integer between 2 and 11; 11:1(n) and where n is an integer between 2 and 10; 10:1(n), and where n is an integer between 2 and 9; 9:1(n), and where n is an integer between 2 and 8; 8:1(n), and where n is an integer between 2 and 8; 7:1(n) and where n is an integer between 2 and 7; and 6:1(n), and where n is an integer between 2 and 6. Considering the configuration of each bond in the general formula: GalNAc-(A→B)GalNAc-(C→D)Glc-(E)-O—R.

A may be 1, 3, 4 or 6; B may be 1, 3, 4 or 6; C may be 3, 4 or 6 whenB=1; C may be 1, 4 or 6 when B=3; C may be 1, 3 or 6 when B=4; C may be 1, 3 or 4 when B=6; D may be 2, 3, 4 or 6 when E=1; D may be 1, 3, 4 or 6 when E=2;

D may be 1, 2, 4 or 6 when E=3; D may be 1, 2, 3 or 6 when E=4; D may be 1, 2, 3 or 4 when E=6.

It is provided a composition for the promotion of plant growth, the said composition comprising a fatty acid glycoside having the general formula:

GalNAc-GalNAc-Glc-O—R, where GalNAc is α- or β-D-N-acetylgalactosamine, Glc-O—R is a molecule of α- or β-D-glucose esterified to a monounsaturated fatty acid (R), where R is selected from 12:1(n) and where n is an integer between 2 and 11; 11:1(n) and where n is an integer between 2 and 10; 10:1(n), and where n is an integer between 2 and 9; 9:1(n), and where n is an integer between 2 and 8; 8:1(n), and where n is an integer between 2 and 8; 7:1(n) and where n is an integer between 2 and 7; and 6:1(n), and where n is an integer between 2 and 6; and an adjuvant. In a preferred embodiment, the adjuvant is nonylphenol ethoxylate or methylated vegetable oils or both of them at the same time. In a preferred embodiment, the composition has a concentration ranging from 0.16 μg/ml to 50 μg/ml of the fatty acid glycoside and a concentration ranging from 0.013% to 0.07% of the nonylphenol ethoxylate compound or a concentration ranging from 0.15% to 1.16% of methylated vegetable oils, or both concentrations at the same time.

It is provided an extraction and obtention process for the aforesaid compound, process that comprises the following steps:
make plant tissue contact an acid medium, under stirring;
centrifuge the extract obtained in the previous step;
divide into fractions by means of preparative chromatography;
the fraction recovered is concentrated and purified through chromatographies.

In a preferred embodiment, the plants belong to the Rosaceae family.

It is provided a method for the prevention of pathogen infections in plants through the use of the aforesaid compound, method that comprises the application of a concentration ranging from 0.03 μg/ml to 400 μg/ml of the said compound, where the application is carried out by spraying or immersion or both things at the same time. In a preferred embodiment, the pathogen may be *Rhodococcus fascians*, *Clavibacter michiganensis*, *Xanthomonas fragariae*, *Colletotrichum* spp, *Penicillum digitaturn*, *Pseudomonas viridiflava*, *C. michiganensis*, *Acidovorax avenae*, *Pseudomonas viridiflava*, *Xanthomonas citri*, *Corynespora cassiicola* and *Botrytis cinerea*, and the plant may be soyabean, strawberry, lemon tree, sugar cane or *A. thaliana*.

It is provided a method for the treatment of pathogen-infected plants through the use of the aforesaid compound, method that comprises applying to a plant a concentration ranging from 20 μg/ml to 400 μg/ml of the said compound, where the application may be performed by spraying or immersion. In a preferred embodiment, the pathogen may be *Rhodococcus fascians*, *Clavibacter michiganensis*, *Xanthomonas fragariae*, *Colletotrichum* spp, *Penicillum digitatum*, *Pseudomonas viridiflava*, *C. michiganensis*, *Acidovorax avenae*, *Pseudomonas viridiflava*, *Xanthomonas citri*, *Corynespora cassiicola* y *Botrytis cinerea* and the plant may be soyabean, strawberry, lemon tree, sugar cane or *A. thaliana*.

It is provided a method for the induction of defenses in plant, by using the compound above described, the said method comprising the application of a concentration ranging from 0.03 μg/ml to 100 μg/ml of the said compound, to a plant.

It is provided a method to promote plant growth by using the compound above described, the said method comprising the application of a concentration ranging from 0.16 μg/ml to 50 μg/ml of the said compound, to a plant. In a preferred embodiment, the plant is soybean, strawberry or sugar cane.

DETAILED DESCRIPTION OF THE INVENTION

The development of agricultural bioinputs of plant origin, such as the compound according to the present invention, have a neat advantage over the bioinoculants used in agriculture, because in the latter the potential risks involved in the release of microorganisms into the environment, that might negatively affect the agroecosystem, have to be assessed. Because of this, the bioactive compounds of plant origin have less restrictions as regards development and registration as agricultural bioinput.

On the other hand, the extraction of such bioactive fatty acid glycosides, in water or alcohols or both media at the same time, constitutes an easy, fast and harmless method, with respect to traditional methods of extraction that employ toxic solvents such as methanol. Besides plant leaves are taken advantage of for the obtention of said glycosides, and those leaves are agricultural waste generated at the end of the cultivation season, unlike many other bioinputs of plant origin that are produced from non-cultivated species such as wild plants or algae species.

It has been shown that the defenses induced through the application of the compound according to the present invention are translocated to other parts of a plant, reducing the development of diseases in the whole plant (systemic action), what was seen in strawberry plants whose fruits exhibited a lesser severity of post harvest diseases.

Figure 1:
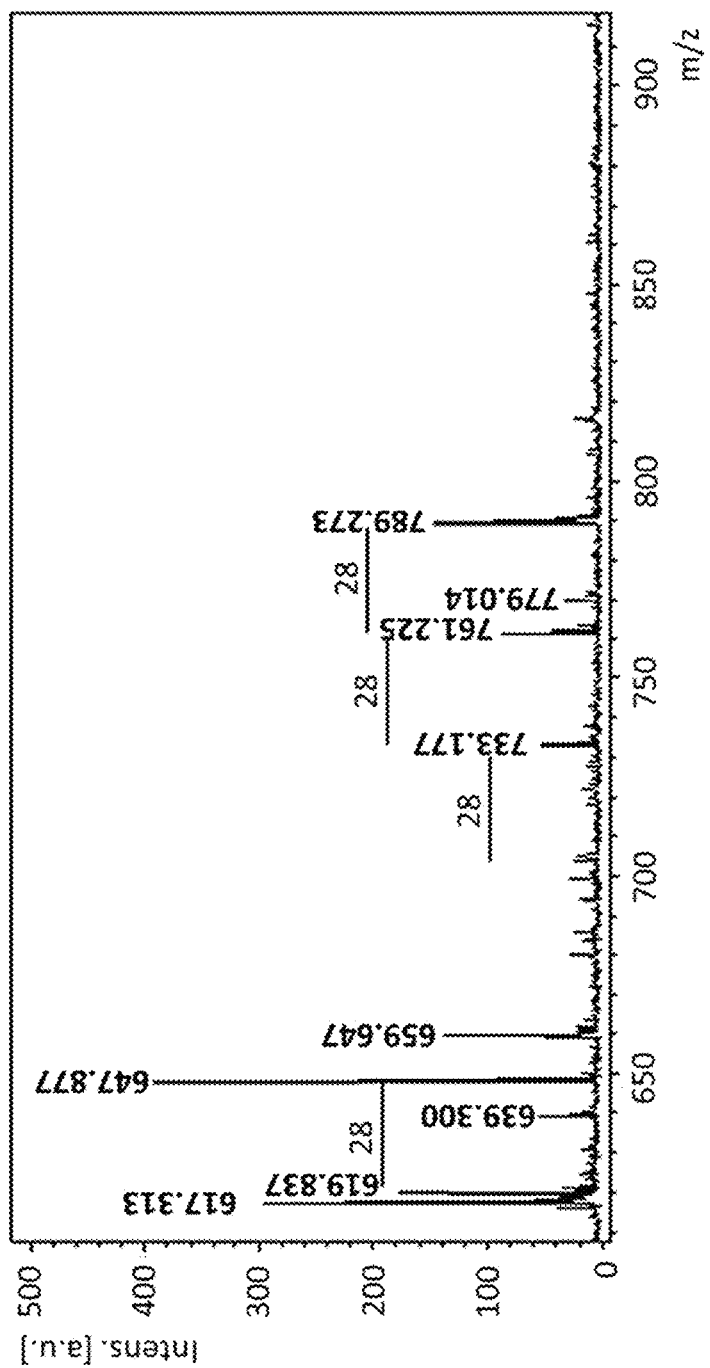
FIG. 1 shows a graph of Analysis by mass spectrometry desorption/ionization-Time of flight (MALDI-TOF) matrix-assisted. The FLs were analyzed by using a matrix of 2.5-dihydroxybenzoic acid (DHB) in positive ion and reflectron mode.

The MALDI-TOF mass spectrum analysis (FIG. 1) showed different signals whose m/z values differed between each other in 28 units, this being a feature of the presence of fatty acids in a chemical structure.

Figure 2:
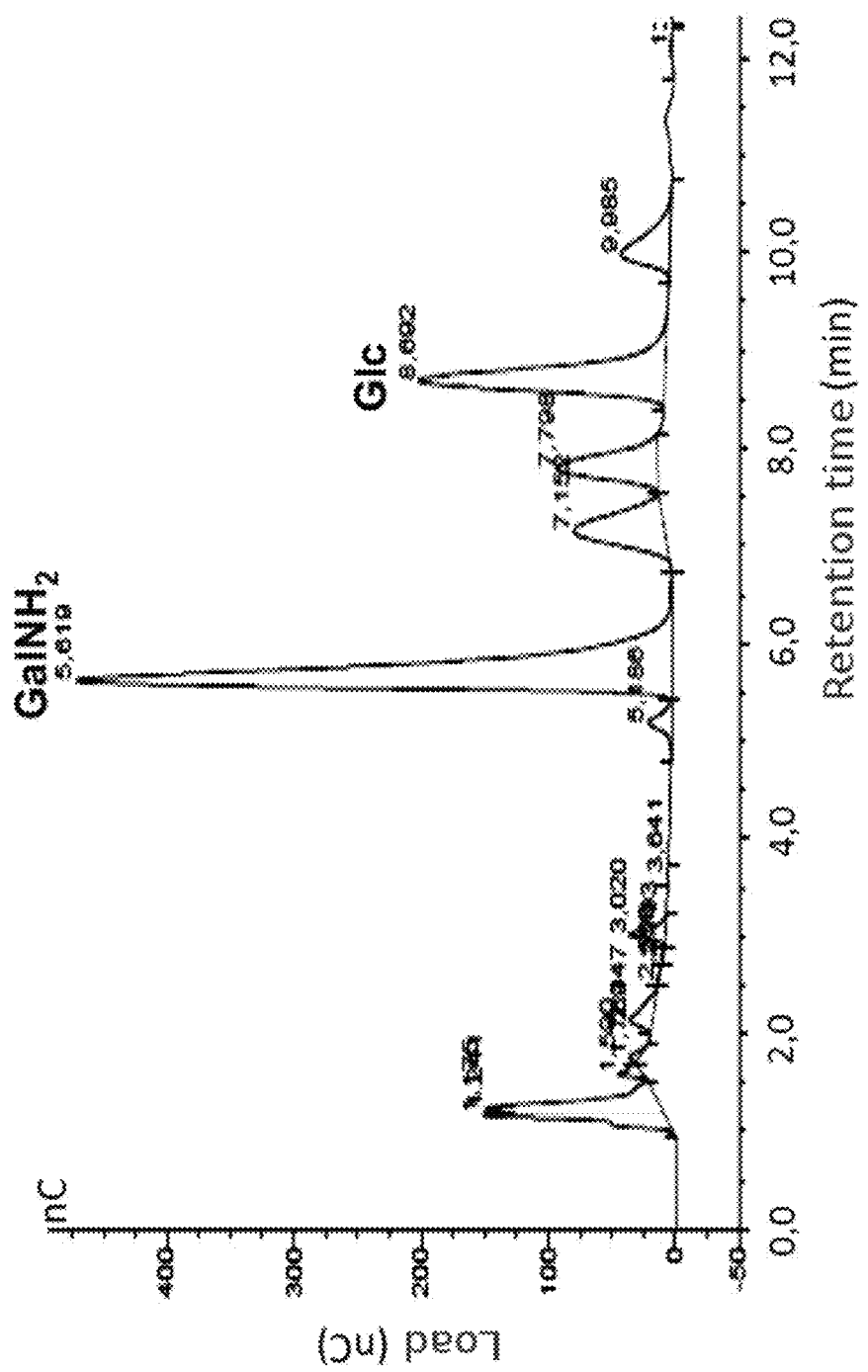
FIG. 2 shows in a graph the composition of the FLs. They were identified by means of HPAEC-PAD of neutral monosaccharides and amino sugars released from FLs acidic hydrolysis. D-galactosamine (GalNH2) and D-glucose (Glc) were the main monosaccharides in the FL molecule.

The analysis of existing monosaccharides released by hydrolysis and identified by HPLC of the FLs showed the absence of acid monosaccharides and the presence of neutral monosaccharides and amino sugars. The two main sugars present in FLs molecules were D-galactosamine and D-glucose (FIG. 2).

The fatty acids present in the FLs chemical structure were released by means of basic hydrolysis, were derivatized and were afterwards analyzed by gas chromatography: the results showed that the FLs are composed of an unsaturated fatty acid that has from 6 to 12 carbon atoms.

Figure 3:
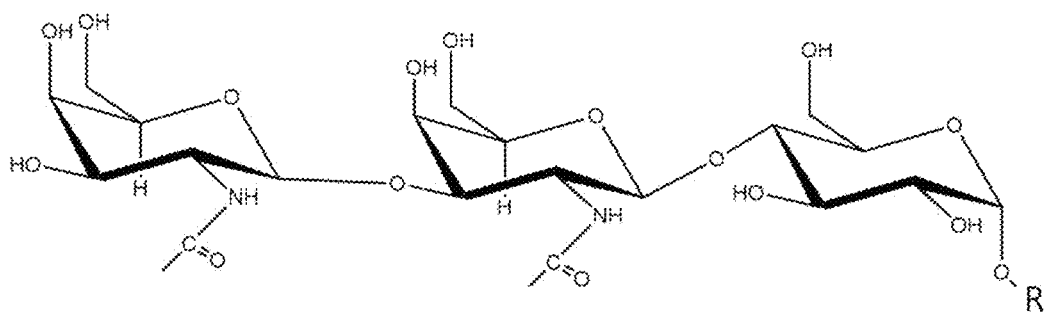
FIG. 3 shows the chemical structure proposed for the FLs, which are fatty acid glycosides comprising two molecules of N-acetylgalactosamine bonded to a single glucose molecule that is esterified with a monounsaturated fatty acid of 6 to 12 carbon atoms (R).

Bearing in mind all of the information from the chemical analysis, the chemical structure proposed for the FLs is a fatty acid glycoside composed of two molecules of N-acetyl-galactosamine bonded to a single unit of glucose that is esterified with a monounsaturated fatty acid having from 6 to 12 carbon atoms (FIG. 3). The molecular weight proposed is 715.12; 727.12; 739.12; 751.12; 763.12; 775.12 and 789,12, that respectively correspond to an R of 6, 7, 8, 9, 10, 11 y 12 carbon atoms.

The new FLs compounds according to the present invention correspond to the general formula.

Considering the configuration of each bond in the general formula:

GalNAc-(A→B)GalNAc-(C→D)Glc-(E)-O—R, where GalNAc is α- or β-D-N-acetylgalactosamine and Glc-O—R is a molecule of α- or β-D-glucose esterified to a monounsaturated fatty acid (R).

R may be:

12:1(n) and where n is an integer between 2 and 11; 11:1(n) and where n is an integer between 2 and 10; 10:1(n), and where n is an integer between 2 and 9; 9:1(n), and where n is an integer between 2 and 8; 8:1(n), and where n is an integer between 2 and 8; 7:1(n) and where n is an integer between 2 and 7; and 6:1(n), and where n is an integer between 2 and 6.

12:1(n), where n may be 2, 3, 4, 5, 6, 7, 8, 9, 10 or 11.
11:1(n), where n may be 2, 3, 4, 5, 6, 7, 8, 9 or 10.
10:1(n), where n may be 2, 3, 4, 5, 6, 7, 8 or 9.
9:1(n), where n may be 2, 3, 4, 5, 6, 7 or 8.
8:1(n), where n may be 2, 3, 4, 5, 6, 7 or 8.
7:1(n), where n may be 2, 3, 4, 5, 6 or 7.
6:1(n), where n may be 2, 3, 4, 5 or 6.

Considering the configuration of each bond in the general formula:

GalNAc-(A→B)GalNAc-(C→D)Glc-(E)-O—R

A, may be 1, 3, 4 or 6; B, may be 1, 3, 4 or 6; C, may be 3, 4 or 6 whenB=1; C, may be 1, 4 or 6 when B=3; C, may be 1, 3 or 6 when B=4; C may be 1, 3 or 4 when B=6; D, may be 2, 3, 4 or 6 when E=1; D, may be 1, 3, 4 or 6 when E=2; D, may be 1, 2, 4 or 6 when E=3; D, may be 1, 2, 3 or 6 when E=4; D, may be 1, 2, 3 or 4 when E=6

For example, FL may have the general formula I

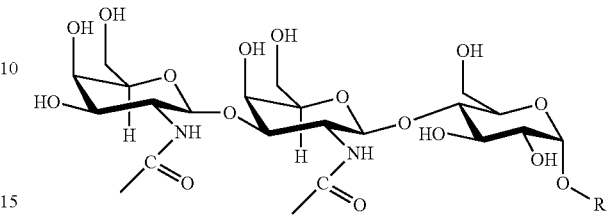

I

Antimicrobial Activity

Different concentrations of FLs (0; 0.025; 0.05; 0.075; 0.1; 0.25; 0.5; 0.75; 1; 2.5; 5; 7.5; 10; 25; 50; 75 and 100 µg/ml) were tested and it was determined the effective concentration that inhibits 50% of a microorganism growth ($CE_{50}$): it was found that even at very low concentrations, the purified compound inhibited the growth of bacteria pathogenic for plants, animals, human beings, as well as plant pathogenic fungi (Table 1). In many cases, the FLs showed an antimicrobial activity that was more effective, when compared to known antibiotics, what was evidenced by a lower $EC_{50}$ value against human pathogens (*Staphylococcus aureus, Staphylococcus epidermidis, Enterococcus faecium* CRL35, *Bacillus subtilis, Listeria monocytogenes, Proteus* sp., *Pseudomonas aeruginosa*) and plant pathogens (*Rhodococcus fascians, Clavibacter michiganensis* subsp *sepedonicus* C5, *Xanthomonas fragariae*). It was found that the FLs were between 10 and 100 times more efficient to inhibit bacteria growth, in comparison with the assessed fungi.

It is important to remark that all of the fungi tested are pathogenic for plants: for example, the *Colletotrichum* spp. strains are pathogenic for strawberry plants; *Penicillium digitatum*, that is a pathogen of lemon tree fruits and *Botrytis cinerea* is a necrotrophic fungus that affects different plant species.

Since the FLs are biodegradable, they can be used in combination with smaller quantities of fungicides that exhibit a certain toxicity. The FL compound might help to reduce, or even replace, the toxic fungicides currently used in strawberry production and other crops and agricultural products.

TABLE 1

FLs antimicrobial activity against diverse bacterial and fungal pathogens, assessed in vitro as $C_{50}$. On the right side column, the $CE_{50}$ values described for other antimicrobial compounds against the assessed pathogens are shown.

| SPECIES | $CE_{50}$ (µg/ml) | $CE_{50}$ (µg/ml) for commercial antimicrobial |
|---|---|---|
| Bacteria | | |
| Gram Positive | | |
| *Rhodococcus fascians* | 0.2 | Erythromycin 0.25 |
| | | Clarythromicin 0.06 |
| | | Azythromicin 0.5 |
| *Clavibacter michiganensis* subsp. *sepedonicus* C5 | 0.3 | Kanamycin 2.5 |

TABLE 1-continued

FLs antimicrobial activity against diverse bacterial and fungal pathogens, assessed in vitro as $C_{50}$. On the right side column, the $CE_{50}$ values described for other antimicrobial compounds against the assessed pathogens are shown.

| SPECIES | $CE_{50}$ (µg/ml) | $CE_{50}$ (µg/ml) for commercial antimicrobial |
|---|---|---|
| Staphylococcus aureus | 0.4 | Vancomycin 0.78 |
| Staphylococcus epidermidis | 0.5 | Vancomycin 1.56 |
| Enterococcus faecium CRL35 | 0.6 | Vancomycin 0.78 |
| Micrococcus sp. | 0.7 | Erythromycin 0.12 Clarythromicin 0.06 Azythromicin 0.12 |
| Bacillus subtilis | 0.8 | Erythromycin 0.25 Clarythromicin 0.12 Azythromicin 2 |
| Listeria monocytogenes | 0.9 | Erythromycin 0.25 Clarythromicin 0.12 Azythromicin 0.5 |
| Gram Negative | | |
| Xanthomonas fragariae | 0.2 | Cecropin B 0.04 |
| Xanthomonas axonopodis pv citri | 0.2 | N/D |
| Pseudomona aeruginosa | 0.4 | Imipenem 0.78 Meropenem 0.2 |
| Proteus sp. | 0.7 | Imipenem 1.56 Meropenem 0.1 |
| Pseudomona syringae pv gladiolii | 1.1 | N/D |
| Pseudomona corrugata | 0.9 | N/D |
| Erwinia carotovora | 2.7 | N/D |
| Citrobacter sp. | 3.2 | Imipenem 0.2 Meropenem 0.02 |
| Escherichia coli MC 4100 | 7.3 | Imipenem 0.1 Meropenem 0.01 |
| Escherichia coli D21 e7 | 8.5 | N/D |
| Salmonella Newport | 10.3 | Imipenem 0.5 Amikasin 2 |
| Escherichia coli D21 | 12.6 | N/D |
| Fungi | | |
| Colletotrichum fragariae F7 | 27.8 | Benomyl 0.29 |
| Colletotrichum acutatum M11 | 25.3 | Captan 1 |
| Colletotrichum gloeosporioides L9 | 29.8 | Benomyl 0.29 |
| Botritys cinerea | 50 | Imazalil 8 |
| Penicillum digitatum | 40 | Imazalil 6 |

It was also ascertained the antimicrobial activity as Minimum Inhibitory Concentration (MIC), through the testing of seriate dilutions of the FLs fraction on solid media plates: the FLs were more active, even at very low concentrations, against bacteria, in comparison with the phytopathogenic fungi assessed (Table 2). The MIC values (mg/ml) were higher than the $CE_{50}$ (µg/ml) ones.

TABLE 2

FLs antimicrobial activity. The minimum inhibitory concentration (CIM, for its acronym in Spanish)) was determined in vitro against phytopathogenic bacteria and fungi.

| SPECIES | CIM mg/ml |
|---|---|
| BACTERIA | |
| Gram positive | |
| Clavibacter michiganensis subsp. sepedonicus C5 | 0.025 |
| Gram negative | |
| Acidovorax avenae | 0.025 |
| Pseudomonas virdiflavo alb8 | 0.025 |
| Xanthomonas citri subsp. citri | 0.05 |
| FUNGI | |
| Corynespora cassiicola | 0.2 |
| Botrytis cinerea BMM | 0.4 |
| Penicillum digitatum P5 | 0.2 |

Figure 4:
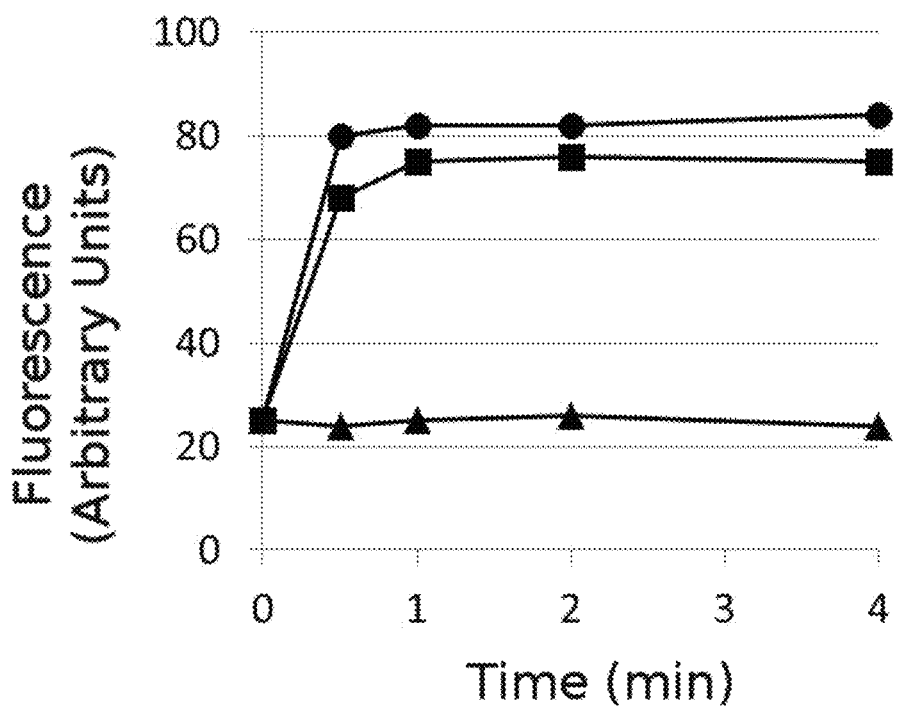
FIG. 4 shows on a graph bacterial membrane permeability. The release of the compound diSC3(5) from the cells treated with 60 μg/ml of FLs (squares), 1.0 μM of Valinomycin (circles) and sterile water (triangles) is shown.

To study the possible mechanism underlying the FLs antimicrobial activity, the effect of the application of FLs upon C. michiganensis cytoplasmic membrane was assessed (FIG. 4), by using the cyanine stain method with 3,3'-Dipropylthiadicarbocianine iodide (diSC3 (5)) (Biochemistry (1999), 38(22), 7235-7242.). The fluorescent compound, diSC3 (5), is sensitive to the dissipation of membrane potential and, as a consequence, an increase of fluorescence is a good indicator of damage inflicted to the membrane: for example, the addition of FLs in a concentration of 60 µg/ml to bacterial cells containing diSC3 (5) induced an increase of fluorescence, that reached its maximum within a minute. The addition of valinomycin 1 µM, a membrane dissipating compound, induced a fluorescence increase similar to the one seen with the FL compound. No changes in the emission of fluorescence were seen in diSC3 (5) C. michiganensis cells in the absence of FLs or valinomycin.

Figure 5:
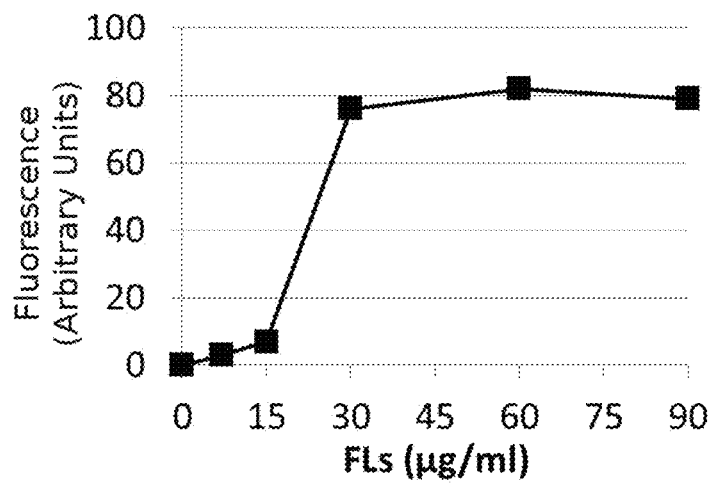
FIG. 5 shows on a graph the dose-dependent effect of FLs (0-90 μg/ml) upon *C. michiganesis* membrane permeability. It is shown the release of the compound diSC3(5) from the cells treated with diverse concentrations of FLs.

On the other hand, changes of potential or the permeability of the plasmatic membrane, or both things at the same time, were dependent on FLs concentration, this indicating a dose-dependent effect (FIG. 5). This effect is clearly noticed when a concentration of the compound FL ranging between 7.5 µg/ml and 90 µg/ml is applied.

Figure 6:
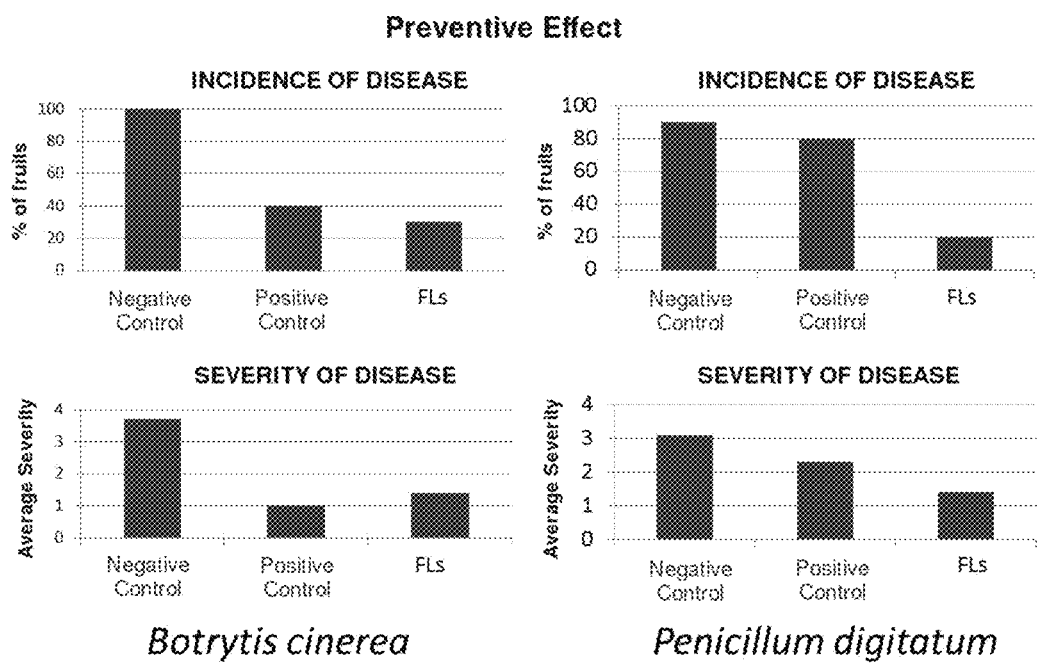
FIG. 6 graphically shows the effects of a pretreatment with FLs (0.1 mg/ml) on the fruits of strawberry plants inoculated with *Botrytis cinerea* and *Penicillum digitatum*. Incidence of the disease (% of fruits with symptoms) and disease severity rate (1: without symptoms; 2: 1-25% of affected area per fruit; 3: 26-50% of affected area per fruit; 4: more than 50% of affected area per fruit), distilled water as negative control and 4% of sodium hypochlorite as positive control.

The FLs compounds are effective as a control agent of postharvest diseases. In particular, the FLs (0.1 mg/ml) showed a preventive and healing effect upon fruits of strawberry plants. The pretreatment with FLs (preventive effect) of strawberry fruits reduced the incidence and the gravity of the gray mold disease, caused by B. cinerea, in a 30% and a 60%, respectively (FIG. 6).

In a similar way, the symptoms of the disease generated by P. digitatum (blue mold) were significantly reduced, with a 78% diminution of the incidence and a 50% diminution of the severity, in comparison with the fruits treated with water. Also assessed were other concentrations of the compound FL (between 0.05 and 0.4 mg/ml), similar results to the preferred concentration of 0.1 mg/ml having been obtained.

Figure 7:
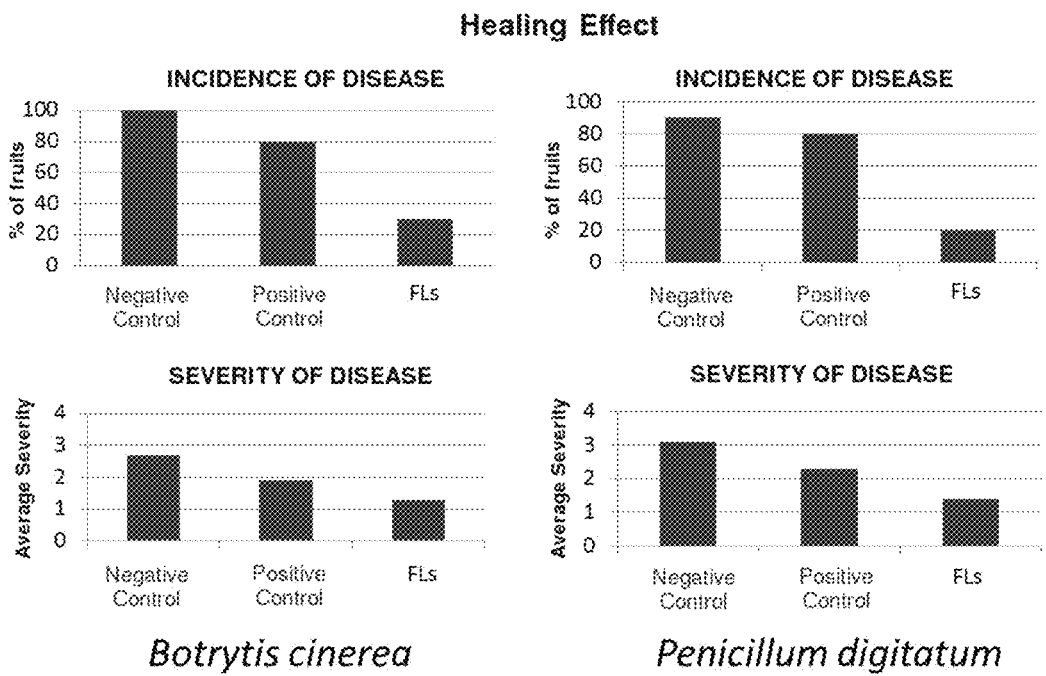
FIG. 7 graphically shows the effects of a treatment with FLs (0.1 mg/ml) on the fruits of strawberry plants previously inoculated with *Botrytis cinerea* and *Penicillum digitatum*. Incidence of the disease (% of fruits with symptoms) and disease severity rate (1: without symptoms; 2: 1-25% of affected area per fruit; 3: 26-50% of affected area per fruit; 4: more than 50% of affected area per fruit), distilled water as negative control and 4% of sodium hypochlorite as positive control.

The application of the FLs compounds (0.1 mg/ml) on fruits previously inoculated with B. cinerea or P. digitatum (healing effect) reduced the incidence of both diseases down to 70%, while the reduction of the severity was 52%, for B. cinerea and 55% for P. digitatum, as compared to control fruits treated with water (FIG. 7).

Tests were carried out, a concentration range of FL between 0.05 and 0.4 mg/ml having been used, with similar results to those obtained with the preferred concentration of 0.1 mg/ml The results from the protection against a disease by means of the treatment with the FLs compounds on fruits of strawberry were better than the results gotten with sodium hypochlorite (disinfectant), that is frequently used in the production of strawberries.

Figure 8:
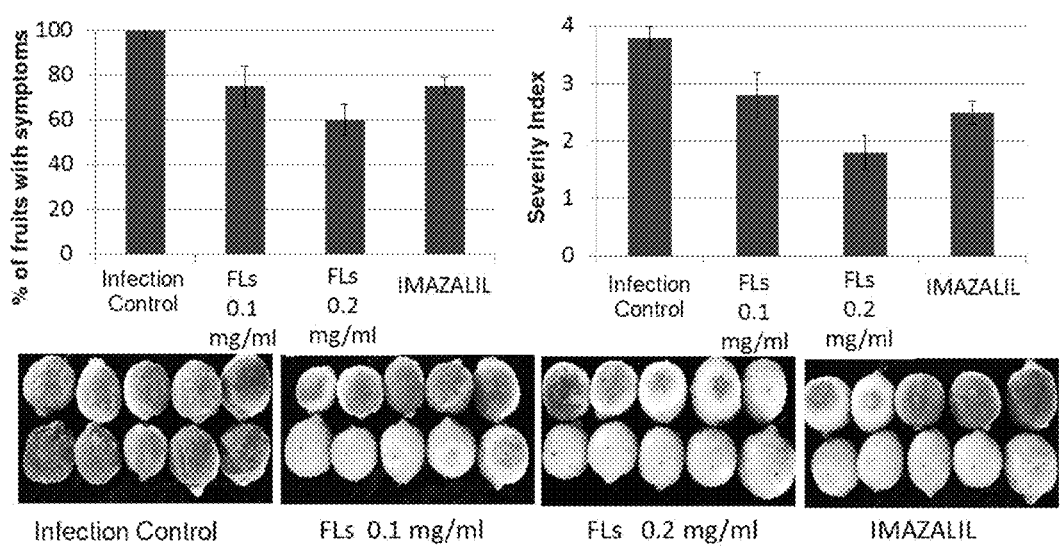
FIG. 8 graphically shows the effects of a pretreatment with FLs (0.1 mg/ml or 0.2 mg/ml) on the fruits of lemon inoculated with *Botrytis cinerea* and *Penicillum digitatum*. Incidence of the disease (% of fruits with symptoms) and disease severity rate (0: without symptoms; 1: 1-25% of affected area per fruit; 2: 26-50% of affected area per fruit; 3: from 51 to 75% of affected area per fruit; 4:76-100% of affected area per fruit), distilled water as infection control, FL (0.1 and 0.2 g/ml) or the commercial fungicide Imazalil (500 ppm).

The FLs compounds showed a preventive effect on treated lemons:

The preventive treatment of the surface of lemons with the FLs compounds lent protection against the infection by *P. digitatum* (FIG. 8). The FLs compounds were applied, for example, at a concentration of 0.1 mg/ml and, as a result, they reduced the incidence and the gravity of the symptoms of the infection with *P. digitatum* in 25% and 26%, respectively. However, when a higher concentration of FLs (0.2 mg/ml) was applied, it was observed a 40% incidence and a reduction of 53% of the gravity of the disease, in comparison with the untreated fruits.

The results obtained for the treatment with the FLs compounds with the use of a preferred concentration of 0.1 mg/ml were comparable to those obtained with Imazalil (a fungicide often used in lemon crops), but the protective effect of FLs was greater when it was applied to the highest concentration of 0.2 mg/ml.

The FLs compounds induce defense systems for the innate immunity and provide a protection against plant diseases.

Figure 9:
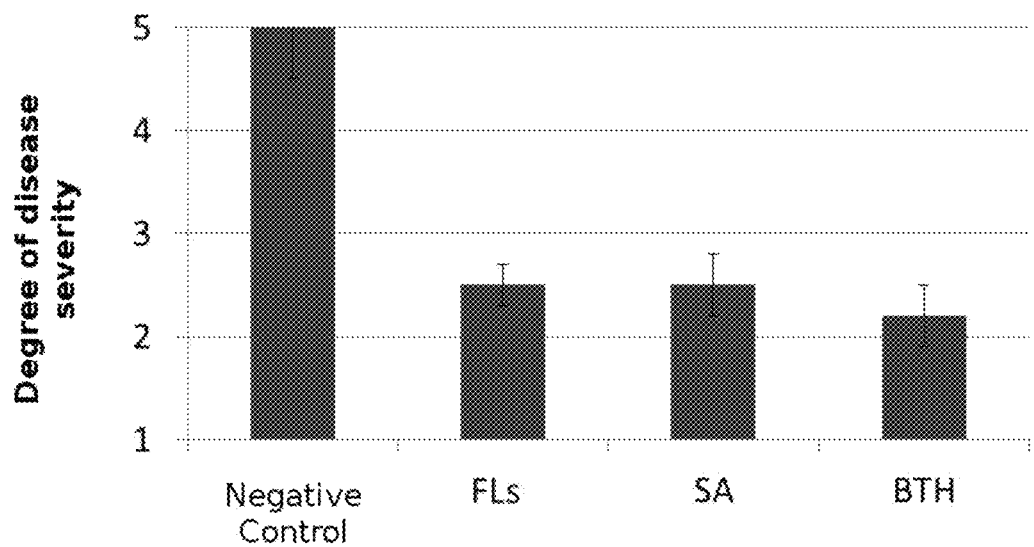
FIG. 9 shows on a graph the results of the induced resistance test (IR) on strawberry plants inoculated with the pathogen *Colletotrichum acutatum*. The plants were sprayed with 0.03 μg/ml of FLs, water (negative control) or known inducers of defenses that include salicylic acid (SA 5 mM) and acibenzolar-s-methyl (BTH 1 mM). 5 days after pretreatment, the plants were inoculated with a virulent strain of the fungus *C. acutatum*. The disease severity index was determined on the petioles of the plants of each treatment (values between 1 to 5 corresponding to the degree of increasing severity).

Strawberry: The Treatment with the FLs Compounds Give Protection Against Anthracnose The plants treated with the FLs compounds showed a 30-40% reduction of the gravity of anthracnose symptoms, as compared to the plants used as control for the disease (FIG. 9). This effect of protection against the disease was comparable to the application of salicylic acid (SA) and acibenzolar-s-methyl (BTH). These results show that the FLs are a proficient ecological alternative for the control of anthracnose in the production of strawberry crops.

The pretratment with the FLs compounds induce a protection against *Pseudomonas viridiflava* alb8, in plants of *A. thaliana*.

Figure 10:
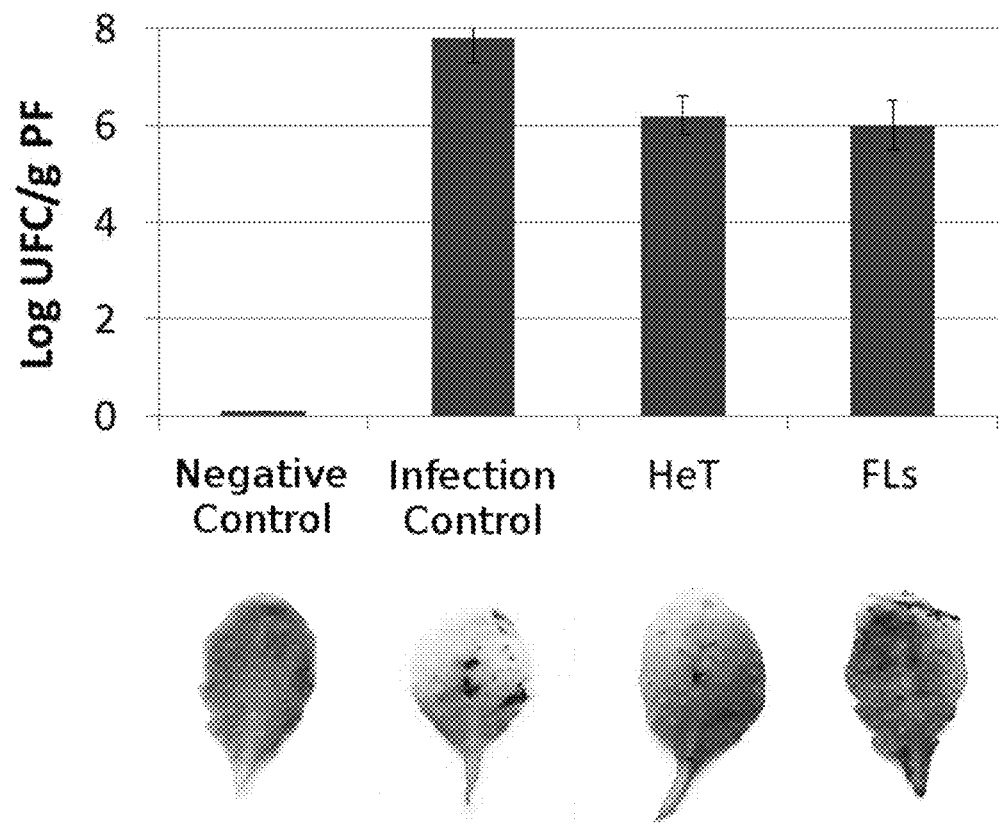
FIG. 10 shows the results of IR tests on *Arabidopsis thaliana* plants with the pathogen *Pseudomonas viridiflava* alb8, previously treated with water (negative control), HeT (57 µg/ml) or FLs (10 µg/ml). Bacterial growth was expressed as a logarithm of colony forming units per gram of leaf weight (log UFC/gPF). The plants not inoculated with the bacteria were used as a negative control of bacterial count.
Figure 11:
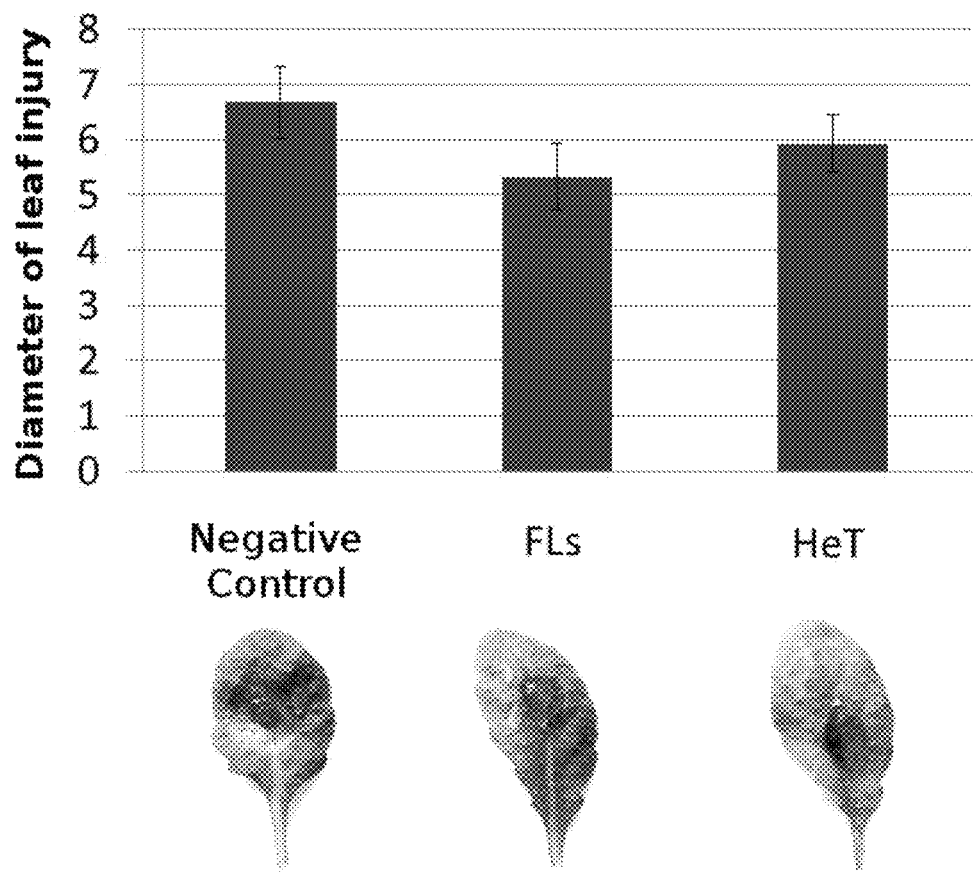
FIG. 11 shows the results of IR tests on *A. thaliana* with the pathogenic fungus *Botrytis cinerea* BMM. Disease severity was determined as the average of leaf-lesion diameter, on infected *A. thaliana* plant leaves pretreated with FLs (10 µg/ml), HeT (57 µg/ml) or water (negative control).

The pretreatment with the FLs compounds in plants of *A. thaliana* induced a clear reduction of the symptoms of the disease caused by the bacterial pathogen *P. viridiflava* alb8 (FIG. 10), this accompanied by a 100-time reduction of the count of bacterial population in infected leaves. Similar results were seen in *A. thaliana* plants infected with *B. cinerea* (FIG. 11), that showed a 33% reduction of the size of the lesion when those plants were treated with the FLs compounds before the infection, while a 16% protection was seen in plants treated with HeT: much less than the ones seen with the FLs compound. In these cases, concentrations ranging from 1 μg/ml and 20 mg/ml of FLs were used, giving a reduction percentage comprised between 15% and 40%.

Figure 12:
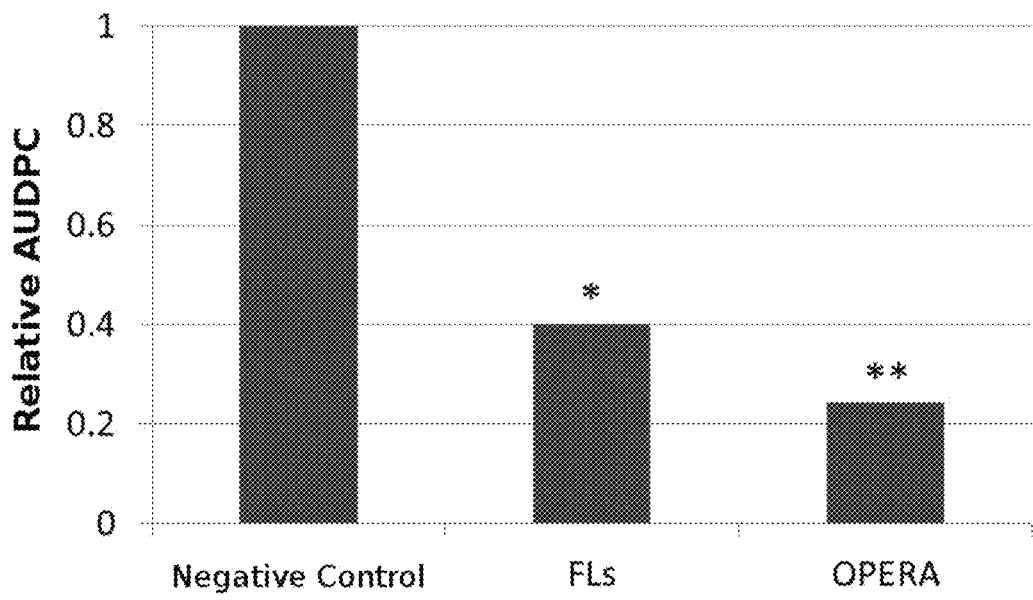
FIG. 12 shows the results of IR test on soyabean plants inoculated with the pathogenic fungus *Corynespora cassiicola*. Disease severity is expressed as the AUDPC (The area under the disease progress curve) with reference to the control plants pretreated with water (negative control), The assessments were performed 4, 7 and 10 days after pathogen inoculation in soyabean plants treated with FLs (0.1 mg/ml) or the commercial fungicide Opera (5 ml/L), 3 days before the inoculation. (*) indicates significant differences with respect to the negative control.

The pretreatment with the FLs compounds gives soybean plants protection against the end-of-cycle disease, ring spot disease, caused by the fungus *Corynespora cassiicola*. Leaf treatment with the FLs compounds three days before the inoculation with a pathogenic strain of *C. cassiicola* brought a significant reduction of the severity (60%) of the disease symptoms in soybean plants (FIG. 12). In comparison, the application of the commercial fungicide Opera (5 ml/L gave, as a result, a 70% reduction of disease severity.

Strawberry: The pretreatment with the FLs compounds provides protection against postharvest diseases.

Figure 13:
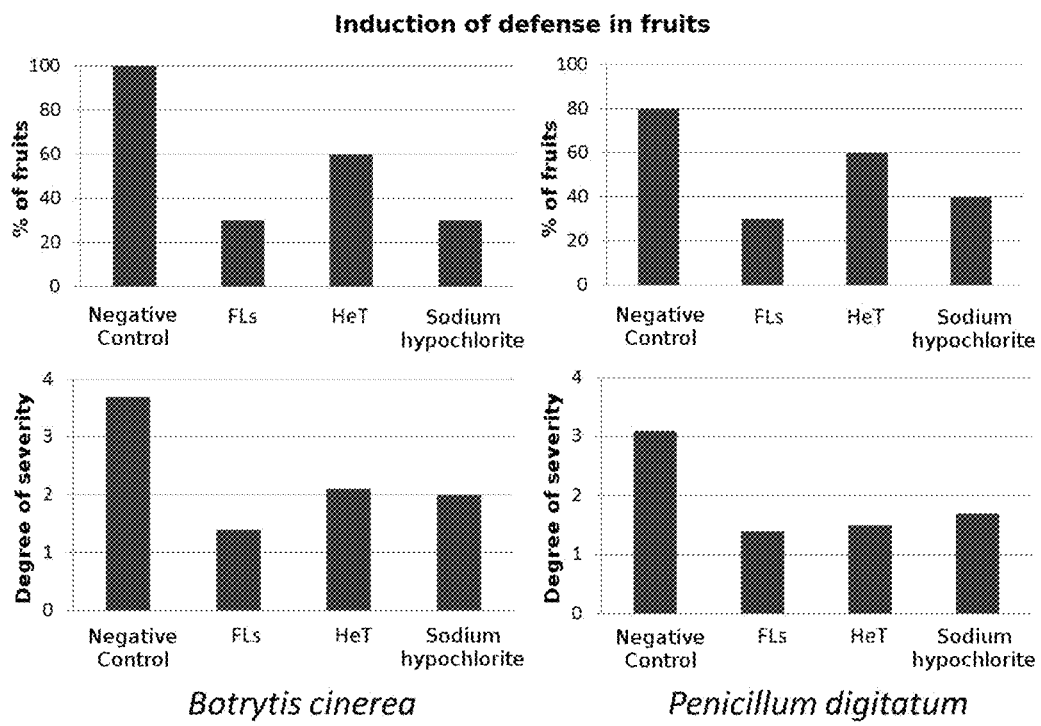
FIG. 13 shows the results of IR test on strawberry fruits treated and later inoculated with *Botrytis cinerea* and *Penicillum digitatum* under conditions of controlled growth. The incidence of the disease was assessed (% of symptomatic fruits) and disease severity rate (1: without symptoms; 2: 1-25% of affected area per fruit; 3: 26-50% of affected area per fruit; 4: more than 50% of affected area per fruit). The disinfected strawberries were immersed into distilled water (negative control) or a solution of FLs (0.01 mg/ml) or HeT (0.8 mg/ml) at pathogen-growth subinhibitory concentrations. As a positive biocide control, a 4% solution of sodium hypochlorite was used.
Figure 14:
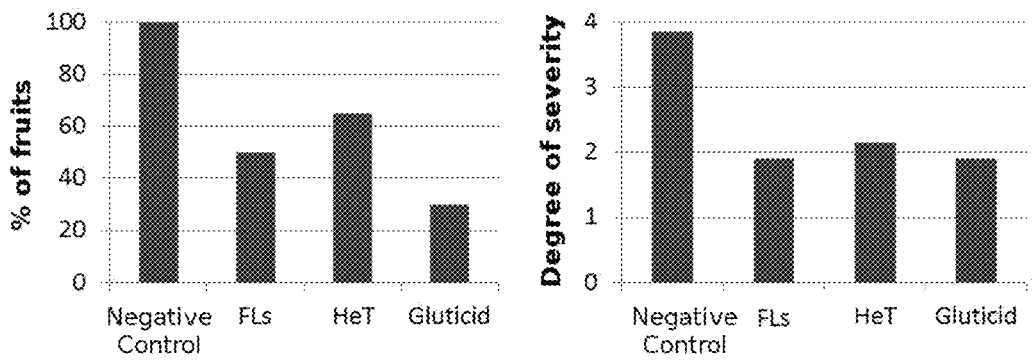
FIG. 14 shows the results of IR test on strawberry fruits against postharvest diseases. The incidence of the disease was assessed (% of symptomatic fruits) and disease severity rate (1: without symptoms; 2: 1-25% of affected area per fruit; 3: 26-50% of affected area per fruit; 4: more than 50% of affected area per fruit) created by natural pathogens originating in the field. The fruits of strawberry plants pretreated with distilled water (negative control) or FLs (0.01 mg/ml) or HeT (0.8 mg/Thml) or the commercial biofungicide Gluticid (3 mg/ml) were assessed.

With respect to strawberry postharvest diseases. The FLs compounds (subinhibitory concentrations for pathogen growth, between 5 μg/ml and 100 μg/ml) had a preventive effect upon the development of the disease, both in experiments held in controlled conditions of growth (FIG. 13) and under the pressure of the natural inoculum in the field (FIG. 14), what suggests the activation in strawberries of the defense systems against pathogens.

The healthy strawberries harvested and disinfected were inoculated, under controlled conditions of growth, with strains of *B. cinerea* (gray mold) and *P. digitatum* (blue mold). The infected fruits were subsequently treated with a 10 μg/ml solution of the FLs compounds, what reduced gray mold incidence and severity in 70% and 62% respectively. A similar result was gotten for blue mold, where a 62% reduction was seen for the incidence and a 60% one for the severity. In comparison, the treatment with HeT reduced the incidence and the gravity of *B. cinerea* in 40% and 45% respectively, and the treatment with sodium hypochlorite diminished the incidence in 70% and the severity in 45%. For blue mold, the treatment with HeT produced an incidence reduction of 25% and a severity reduction of 50%, while sodium hypochlorite reduced the incidence in 50% and the severity in 40%.

The in-field experiments performed om strawberry plants using a conventional agricultural management showed that the on-leaf application of a solution of the FL composition in a pathogen subinhibitory concentration (between 5 μg/ml and 100 μg/ml; preferably, 10 μg/ml) reduces the incidence and the severity of postharvest diseases in the fruits of plants treated with FLs, in up to 50%. In comparison, the application of the commercial bioproduct Gluticid, a fungicide and inducer in plants of defenses against pathogens, reduced the incidence of postharvest diseases in 70%. However, the preventive effect of the FL had a longer duration than Gluticid's and, as a consequence augmented the commercial life of fruits.

Figure 15:
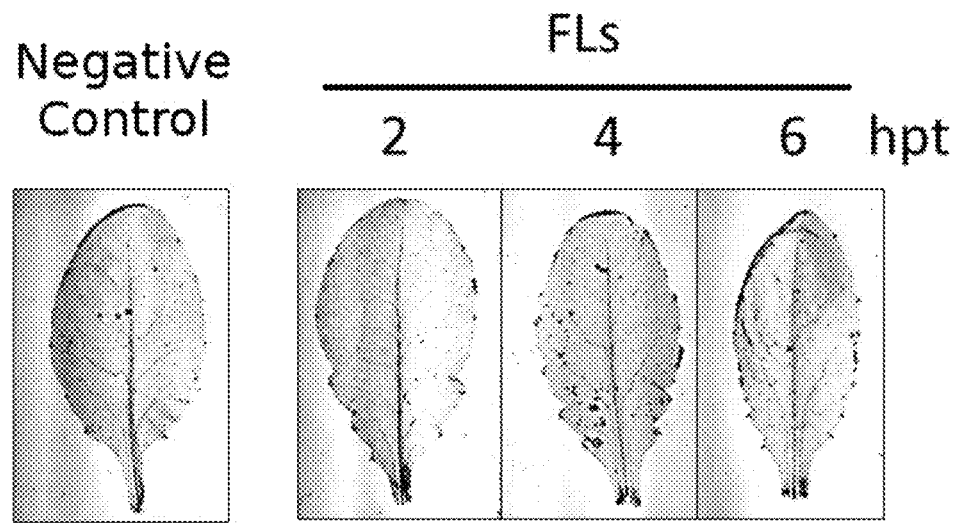
FIG. 15 shows photos of the production of superoxide radicals in *A. thaliana* plant leaves. The staining with NBT, seen as dark spots (purple), indicates the accumulation of the superoxide radical. The plants were treated with distilled water (negative control) or FLs (0.01 mg/ml). The leaves were stained 0, 2, 4 and 6 horas after treatment (hat)

Production of oxygen reactive species in *A. thaliana* leaves: The leaf treatment of *A. thaliana* plants with a solution of the FLs compounds induced an early and transient accumulation of the superoxide radical ($O_2\cdot^-$) (FIG. 15) in the leaves, which was seen as dark spots (purple). The superoxide production reached a maximum accumulation 4 hours after the treatment, what is in agreement with an early oxidative outbreak as a typical signal of an innate activation of a defense against pathogens.

Figure 16:
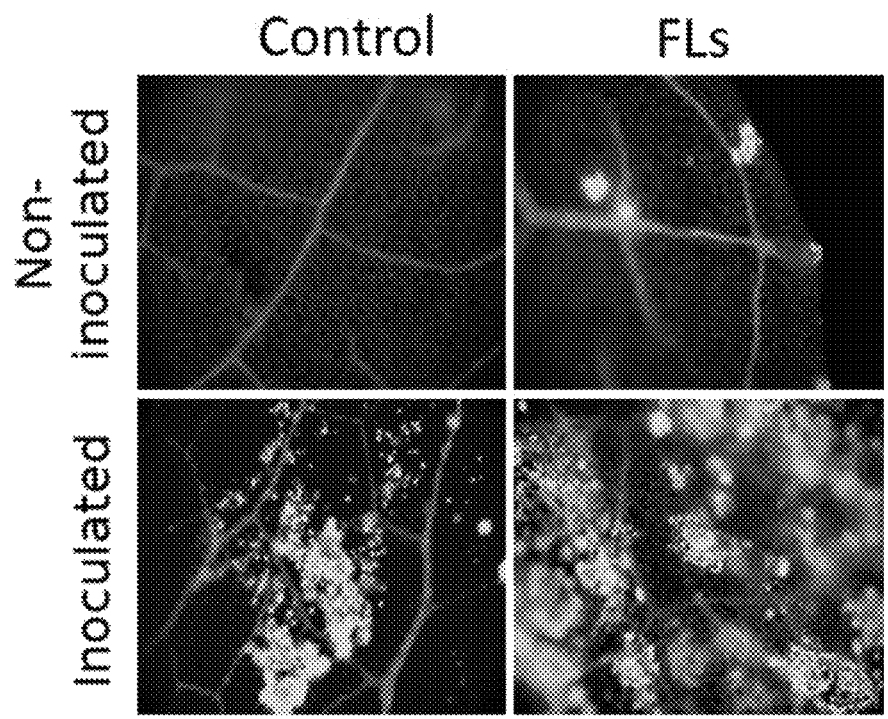
FIG. 16 shows photos of callose deposits in *A. thaliana* leaves, as seen with aniline blue staining; callose deposits are seen as shining spots, when a fluorescent microscope with UV light is used. *A. thaliana* plants were pretreated with water (control) or FLs (0.01 mg/ml) and 6 days later were stained with aniline blue. Besides, a group of pretreated plants with water or FLs was inoculated with *P. viridiflava* 4 days after treatment and stained with aniline 2 days after inoculation.

Accumulation of callose in leaves treated with the FLs compounds: The accumulation of callose is a plant defense mechanism that reinforces the cell wall and helps to prevent the invasion by pathogens. It has been shown that *A. thaliana* leaves treated with the FLs compounds only create a weak deposition of callose (FIG. 16, upper right photo), but the accumulation was very prominent when the FLs-treated plants were afterwards challenged with the pathogen *P. viridiflava* alb8 (FIG. 16, lower right photo). No accumulation of callose was detected in the plants treated with water and not inoculated (FIG. 16, upper left photo). It is interesting to see that the plants treated with the FLs accumulated a much greater quantity of callose when they were inoculated with *P. viridiflava*, in comparison with plants infected and pretreated with water (FIG. 16, lower left photo). This result indicates a possible priming effect that is, the activation, associated with the treatment with FLs, of the alert status against pathogens.

Figure 17:
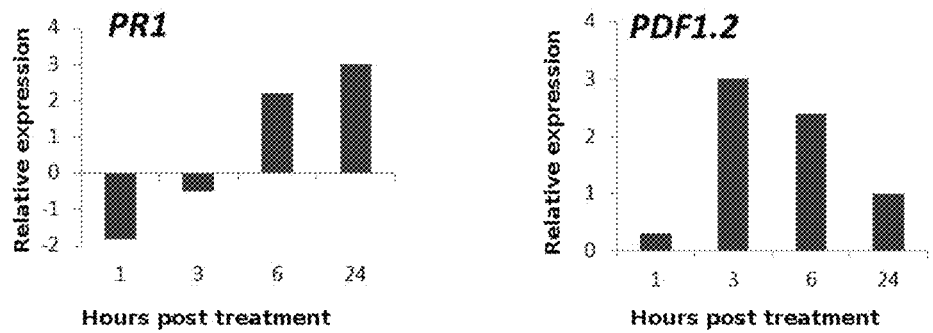
FIG. 17 shows the levels of defense gene relative expression in *A. thaliana* plants, by using the qPCR technique. The levels of expression of PRI genes (salicylic dependent) and PDF1.2 (ethylene/jasmonate dependent) were determined 1, 3, 6- and 24-hours posttreatment with FLs (0.01 mg/ml) in *A. thaliana* leaves. The expression was established in connection with the control plants treated with distilled water. The EFI constitutive expression gene was used in all cases as qPCR-reaction loading control.

Induction of the genetic expression in *A. thaliana*: In *A. thaliana* leaves, the levels of relative expression of the gene PRI, genetic marker associated with the salicylic acid defense way, increased 6 and 24 hours after the treatment with the FLs compounds. Besides, the expression of the gene PDF1.2, genetic marker associated with the signaling of ethylene jasmonate, was induced earlier than PRI's and reached a maximum of expression 3 hours after the treatment with the FLs compounds (FIG. 17).

These results show that the FLs activate more than one way of defense in plants, what indicates that they activate a wide spectrum of protection against pathogens. The difference noticed in the temporal expression of PR1 and PDF1.2, is probably dependent on the antagonistic effect between the salicylic acid defense way and those ways of ethylene jasmonate (Plant Physiology, (2008), 147(3), 1358-1368).

Figure 18:
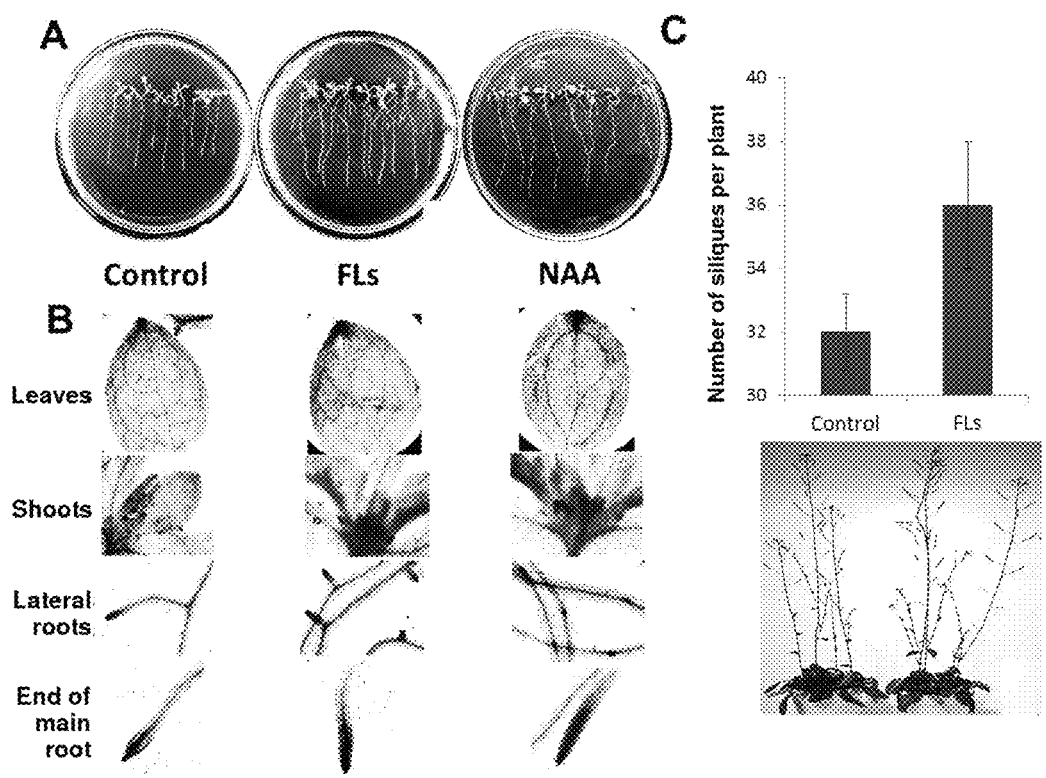
FIG. 18 shows the results of FLs stimulation on *A. thaliana* plants growth: (A) development of *A. thaliana* seedling roots in vitro grown in MS medium supplemented with 0.16 µg/ml of FLs, 0.5 ng/ml of naphthalene acetic acid (NAA), or control plants grown in MS medium, 14 days after germination. (B) expression of auxin dependent DR5: GUS gene, seen as dark spots in *A. thaliana* seedlings grown in medium supplemented with FLs (0.16 µg/ml) or NAA (0.5 ng/ml), compared with control plants 10 days after germination. (C) quantity of siliques per plant, 5 weeks after the treatment carried out by leaf spraying with FLs (1.6 µg/ml) or water (control).

The FLs promote the growth and development of plants: Effect of the FLs upon *A. thaliana* plants growth and development To assess the effect of FLs compounds upon plant growth and development, in vitro growth tests were carried out with the utilization of *A. thaliana* seedlings on agar plates virtually oriented. As shown in FIG. 18A, the FLs in MS culture medium at a concentration of 0.16 µg/ml promoted the elongation of the primary root and stimulated the development of lateral roots in the *A. thaliana* seedlings, as compared to the plants treated with water (control). A similar result was obtained as regards the root development of plants treated with the NAA auxin at 5 ng/ml, although a smaller elongation and development of lateral roots was seen. It is a known fact that auxin is required for the emergence and the development of lateral roots in plants (*The Plant Cell*, (2001) 13(4), 843-852; *The Plant Journal*, (2002) 29(3), 325-332; Cell, (2003) 115(5), 591-602) and it was because of this that it was studied the effect of FLs compounds in *A. thaliana* DR5::GUS transgenic line, in which tissues reacting to an auxin get stained in blue as a consequence of the highly auxin-sensitive synthetic promoter DR5 regulator of the gusA gene. As shown in FIG. 18B, the *A. thaliana* DR5::GUS seedlings that were grown in MS medium supplemented with 0.16 µg/ml of FLs or with 5 ng/ml of NAA exhibited a strong staining (dark blue) in the leaf tips, shoots (probably in stipules), points of lateral roots and lateral root primordia, tips of main roots (probably vascular tissues and columella tissues. As expected, it was observed the staining of those same tissues in *A. thaliana* seedlings not treated, because of auxin endogenous effects, but much less marked when compared to plants treated with FLs or NAA (FIG. 18B).

Besides, the application on leaves of *A. thaliana* mature plants of 1.6 µg/ml of FLs produced an important increase of siliques per plant (12%), as well as in the quantity of main and secondary sterns, in comparison with the control plants treated with water (FIG. 18C).

The FLs compounds promote plant growth and development

Strawberry: Fruit throughput in field conditions.

Figure 19:
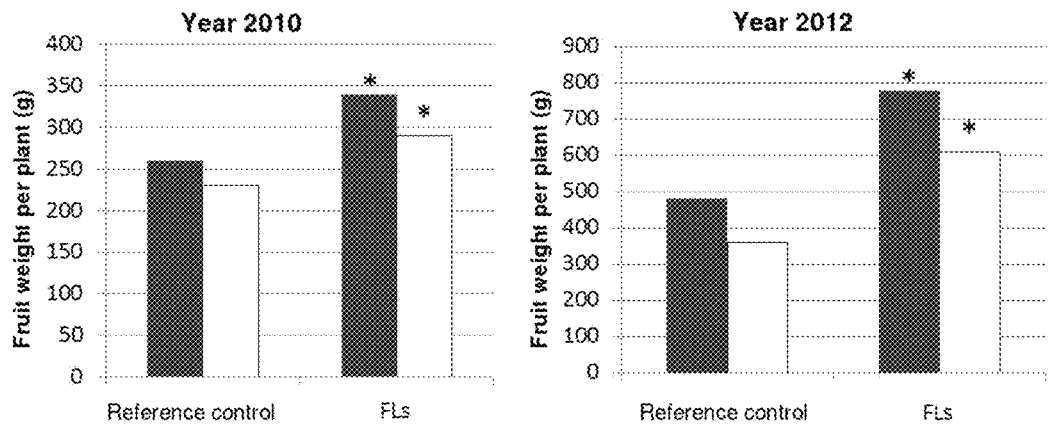
FIG. 19 shows the results upon the throughput of fruits of strawberry plants grown in the field and treated with FLs. The effect of the application of FLs (50 µg/ml) by leaf spraying on a monthly basis upon throughput, was assessed through the collection of the ripe fruits every two weeks from plants grown in the field. The total weight of fruit per plant (gray bars) and commercial (white bars) was established in the seasons (June through November) corresponding to the years 2010 and 2012. Plants treated with distilled water were used as a reference control. In addition, all of the plants received a conventional agronomic handling. (*) indicates significant statistical differences with respect to the control.
Figure 20:
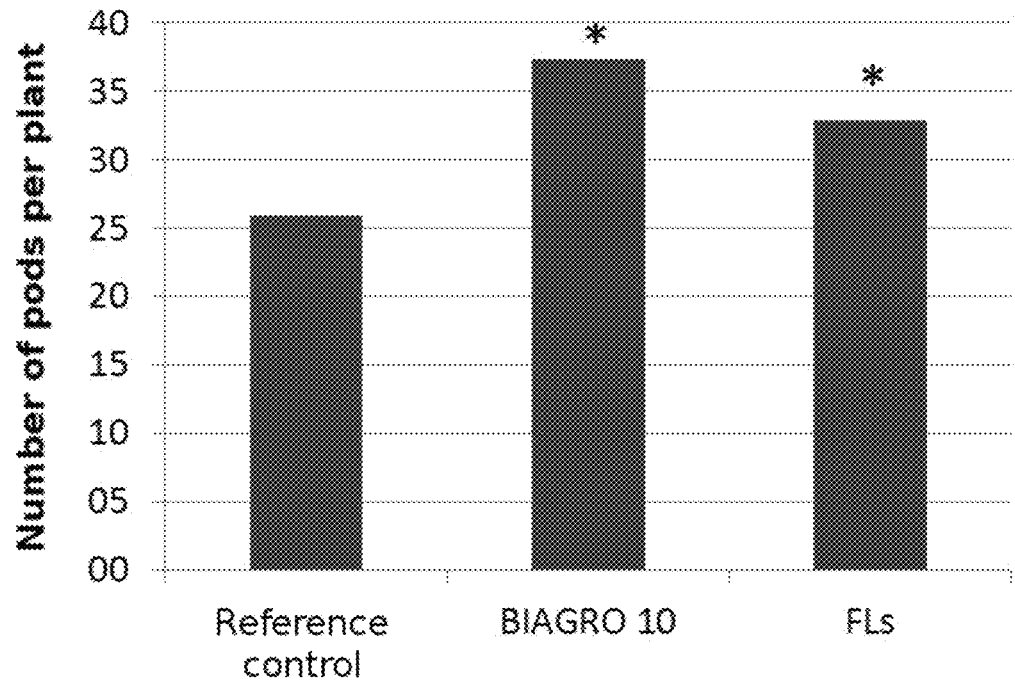
FIG. 20 shows the results upon the development of the pods of soybean plants grown in a greenhouse. The part of the plants above ground was sprayed with water as a reference control, or FLs (50 µg/ml) the moment the plants reached the V1, V7, R1 and R3 stages. When the plants reached the final stage of development R8, the quantity of pods was established. As a positive control was used a treatment upon seeds with the commercial bioinoculant BIAGRO10, based on strains of *Bradyrhizobium* sp. that form nodules in soybean plants with a nodulation promoter *Bradyrhizobium* sp was used as positive control. (*) indicates significant statistical differences with respect to the reference control.

Leaf application of the FLs compounds on strawberry plants grown in the field by using a conventional agricultural management significantly promoted the vegetative growth above ground and increased the total quantity of fruits per plant in approximately 30% and 73% in 2010 and 2012 respectively (FIG. 19), in comparison to the reference plants treated with water. In addition to the total throughput of fruit, the FLs increased the quantity of commercial fruits in approximately the same figures, 20% (2010) and 73% (2012). FL concentrations ranging between 5 µg/ml and 100 µg/ml were applied, the preferred concentration having been 5 µg/ml Effect upon pod production in soybean plants: In greenhouse conditions, soybean plants treated with the FLs compounds developed an 18-36% greater number of pods per plant, than the plants treated with water (FIG. 20). The result gotten was comparable to the treatment of seeds with the commercial bioinoculant BIAGRO10. FLs compounds may be useful as complements of commercial inoculants for soybean based on growth promoter microorganisms.

Figure 21:
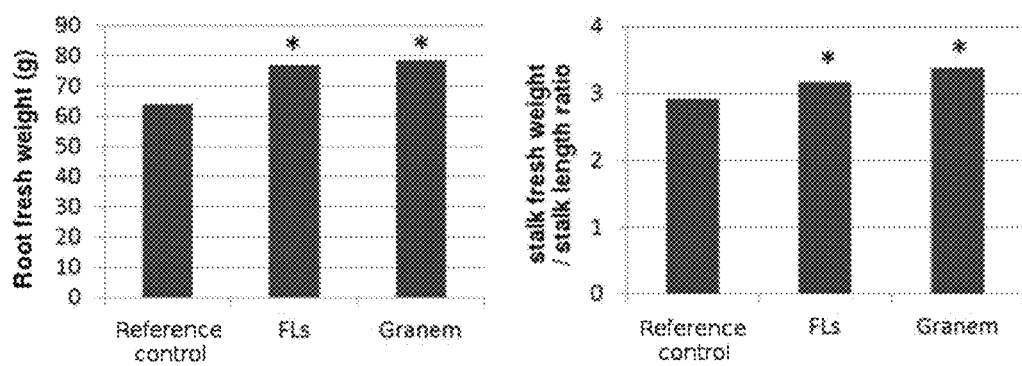
FIG. 21 shows the results upon growth promotion of sugar canes grown in a greenhouse. Uninodal sugar cane stalks were immersed in distilled water (reference control), FLs (14 mµ, or the commercial bioinoculant Granem (based on *Azospirillum* sp. strains) and afterwards were planted in pots with a solid substrate. Two months after having been planted, the canes were treated by leaf spraying with distilled water or FLs (14 µg/ml), respectively. Two months later, the fresh root weight and the stalk length were ascertained. The treatment with Gramen was carried out following the manufacturer's recommendations. (*) indicates significant statistical differences with respect to the reference control.

Promotion of root growth in sugar cane plants grown in greenhouse: The experiments carried out on sugar cane plants grown in a greenhouse (FIG. 21) showed that the application of the FLs compounds promoted the development of biomass of root fresh weight in around 20%. The treatment with FLs also increased the ratio between stem weight and its length in 8.5%, this indicating an important increase of stem thickness. The growth of the stem induced by the FLs was comparable to the effect observed for sugar cane plants treated with the commercial bioinoculant Gramen.

The present invention has activities that are antimicrobial, inducer of plant defenses, promoter of plant growth and augmenter of throughput and plant biomass, to be used in the formulation of biological assets having a potential utilization in agronomy (phitosanitary management, biofertilization, increase of the throughput and augmentation of the biomass), in food preservation and in health, both human and animal. Said activities were not described previously for these compounds in particular.

Antimicrobial activity through the alteration of the functionality of the plasmatic membranes of microorganisms, by reducing the consumption of oxygen, dissipating the potential and increasing the permeability of the plasmatic membranes of those microorganisms. The FLs compounds of the present invention are active against plant pathogens, because of which they can be used to reduce the development of plant diseases and delay the rotting of fruits at room temperature, a fact that was ascertained in strawberries and lemons and can be used for food preservation as well. They are also active against pathogens of human beings and animals, because of which they can be utilized for the development of drugs for the control of microbial diseases.

Inducer activity of plant defenses: The application of the compounds according to the present invention at subinhibitory concentrations with respect to the growth of the pathogen being dealt with, and if the application is performed before the inoculation or the arrival of the pathogen (depending on whether the experiments are performed under controlled conditions or in the field) or during the onset of symptoms of the plant disease, reduces the severity of the diseases.

The induction of the defense was characterized both biochemically and molecularly. Defense mechanism that include the accumulation of reactive oxygen species, the accumulation of callose, the induction of genes related to plant immunity (PR21 PDF1.2) that respond to plant hormones salicylic acid and ethylene jasmonate, were activated.

By way of example, the present composition reduces the symptoms of the disease caused by the bacterial pathogen *Pseudomonas viridiflava* alb8 in *A. thaliana* and the fungi *Colletotrichum acutatum* and *Corynespora cassicola* in strawberry and soybean respectively. The immunity is transferred from the plant to its fruits, a fact that is evidenced by a reduction of the development of postharvest diseases, and reduces diseases created in strawberries by the fungal necrotrophic pathogen *Botritys cinerea*.

The compound according to the present invention has an activity that promotes plant growth or increases the throughput o does both things at the same time. For example, in strawberry plants it increased the vegetative growth and the quantity and quality of the fruits. In soybean, increased the quantity of pods per plant. In sugar canes and *A. thaliana*, increased root development. Directly or indirectly, this activity induces an increment of agricultural throughput, as well as the total plant biomass, what might be taken advantage of as a substrate for the generation of energy.

At concentrations ranging between 0 µg/ml and 400 µg/ml, the FLs compounds have an antimicrobial activity:

In strawberries they delay the rotting of fresh fruits caused by pathogens, thus extending the preservation of said fruits at room temperature, through a direct application on the fruit surface.

In lemons they delay the rotting of fresh fruits caused by parhogens, thus extending the preservation of said fruits at room temperature, through a direct application on the fruit surface.

They are effective against the potato pathogen *Clavibacter michiganensis* subsp. *Sepedonicus* C5; the strawberry pathogens *Xanthomonas fragariae*, *Colletotrichum fragariae*, *Colletotrichum acutatum* and *Colletotrichum gloeosporioides*; and against *Rhodococcus fascians*, a pathogen of diverse plant species, because of which they are effective for the control of different plant pathogen-produced diseases.

They are effective against the pathogens of human beings *Staphylococcus aureus*, *Staphylococcus epidermidis*, *Enterococcus faecium*, *Bacillus subtilis*, *Listeria monocytogenes*, *Pseudomona aeruginosa* and *Proteus* sp., because of which an adequate dosing would permit the development of drugs to be used in human and veterinary medicine. They could also be used as food preserving agent.

At concentrations ranging from 0.03 µg/ml to 0.1 mg/ml, the FLs compounds have an activity that induces plant defenses:

In *A. thaliana* plants they prevent the development of diseases caused by bacterial and fungal pathogens, what suggests the activation of defenses against a wide spectrum of pathogens.

In strawberry plants they prevent the development of anthrachnose and the protection is transferred to the fruits, what reduces the development of postharvest diseases and delays fruit rotting The application on soybean plants before the arrival of a pathogen or during the development of the disease reduces the ringed spot caused by the fungus *Corynespora cassicola*.

At concentrations ranging from 0.16 µg/ml to 50 µg/m, the FLs compounds have an activity that promotes plant growth:

In strawberries they increased the vegetative growth, and the quantity and the quality of the fruits per plant.

In soybean they incremented the quantity of pods per plant, with the potential of increasing the grain throughput per plant.

In sugar canes and in *A. thaliana* they increased root development, favoring the utilization of ground nutrients and having the potential to be an alternative for abiotic stress management, especially hydric stress. This may also entail an increase of agricultural throughput and sugar throughput in sugar canes.

The increase of vegetative growth in energy crops (such as sugar cane) means a greater availability of raw matter for the generation of energy as an alternative to the use of fossil origin fuels.

The application through root in soybean plants functions as a biofertilizer in a direct way, and as a biostimulant in an indirect way, since the compounds disclosed in the present invention are structurally similar to nodulation signals.

The present invention is better illustrated according to the following examples, which should not be deemed to be a limitation imposed on the scope of the invention: on the contrary, it must be understood clearly that other embodiments, modifications and equivalents of the invention may be resorted to, after the reading of the present description might have suggested them to those people skilled in this art, without departing from the spirit of the present invention or from the scope of the appended claims or from these two at a same time

EXAMPLES

Example 1

FLs Purification Protocol

The FLs compounds were obtained from different tissues of crop species of the genuses *Fragaria*, *Duchesnea*, *Potentilla* and other genuses pertaining to the Rosaceae family. The extraction of FLs was carried out in an aqueous medium acidified with trifluoroacetic acid (TFA), homogenizing the plant material (0.1 g of fresh weight//ml of solvent) and stirring at 20 rpm (4° C.) for 2 hours. After centrifugation, the clarified extract was recovered at 10,000×g, 15 min. and was divided into fractions by preparative chromatography, being used a solid phase extraction cartridge (SPE) that contained 10 g of C18-E matrix (Phenomenex, EE. UU.). 20 ml of clarified extract were loaded into the column and afterwards a washing with 80 ml of TFA at 0.1% diluted in water was performed. The initial volume load, together with the washing flow were collected as a preliminary purification stage, because the column molecule does not absorb FLs molecules The fraction recovered (about 80 ml) was concentrated 40 times (2 ml) in a vacuum concentrator (SpeedVac, Thermo Scientific) and was additionally purified by means of HPLC using a reversed phase chromatography column (SOURCE 5RPC, GE Healthcare Biosciences AB). Once again, as in the case of the SPE column, the FLs do not interact with the reversed phase matrix and so they pass through the column, together with the TFA 0.1% diluted in water. The flow fraction collected (2 ml) was concentrated in vacuum conditions up to dryness.

The dry concentrate from the reversed phase column was dissolved in 1 ml of water and was applied to an HPLZ Zorbax-Amino (Waters, EE.UU.) normal phase column. The elution of the united material was performed using an isocratic gradient with 80% of acetonitrile and a flow of 1 ml/min. The desired fraction was collected after 5 minutes approximately, concentrated under vacuum up to dryness and resuspended in 1 ml of water. In a final purification stage it was used a high-performance anion exchange chromatography system with an amperometric detector (HPAEC-PAC) with a Carbopac PA-1 column (4×250 mm, Dionex, EE. UU.) and the FLs were eluted by means of a gradient of a tripartite solvent (200 NaOH mM as solvent A, water as solvent B and AcONa 1M as solvent C). An initial solvent gradient of 25% A, 75% B and 0% C was kept for 10 minutes, followed by a linear gradient that changes the concentrations of solvents B and C up to reaching, after 30 minutes, a final solution that contains 25% A, 25% B and 50% C. The flow rate was 1 ml per minute and the pure FLs were recovered 6.49 minutes later.

Example 2: Chemical Structure of FLs Compounds

Analysis by mass spectrometry desorption/ionization-Time of flight (MALDI-TOF) matrix-assisted: the pure fraction of FLs obtained by HPLC chromatography was neutralized with acetic acid, concentrated in vacuum conditions up to dryness and analyzed by means of mass spectrometry (MALDI-TOF), a 2,5-dihydroxybenzoic (DHB) acid matrixin positive ion and reflectron mode having been used.

Composition in monosaccharides: the pure fraction of FLs was concentrated up to dryness in a vacuum concentrator (SpeedVac, Thermo Scientific), was dissolved in distilled water and hydrolyzed in trifluoroacetic acid (TFA) for 4 hours at 100° C. The hydrolyzed sample was concentrated again in vacuum conditions up to dryness, dissolved in distilled water and analyzed by HPLC to identify released monosaccharides, in comparison with standard samples of D-galactosamine, D-glucosamine, L-fucose, D-mannose, D-galactose and D-glucose. The analysis was carried out by means of high-performance anion exchange chromatography with pulsed amperometric detection (HPAEC-PAC), a Carbopac P20 column (3×150 mm, Dionex, EE. UU.) anion exchange column having been used, and a flow of 0.5 ml per minute. Neutral monosaccharides were eluted by means of an isocratic program of 6% of solvent A (NaOH 200 mM) and 94% of solvent B (distilled water). Acid monosaccharides were eluted by means of a tripartite solvent (NaOH 200 mM as solvent A, water as solvent B and AcONa 1M as solvent C), an isocratic program of 24% of A, 62% of B and 14% of C having been used.

Composition in fatty acids: fatty acids were determined by means of methyl ester derivatives gas chromatography. The pure fraction of FLs obtained by HPLC was hydrolyzed in NaOH 1.67% at room temperature and stirred for 24 hours. Afterwards it was acidified with HCl and extracted three times with an equal volume of dichloromethane. The organic phases were recovered, grouped together and concentrated up to dryness. The resulting residue was dissolved in 0. ml of toluene and an equal volume of boron trifluoride at 20% in methanol was added. The dissolved sample was incubated at 80° C. for 1 h under a nitrogen atmosphere. After cooling at room temperature, the sample was washed three times, adding an equal volume of distilled water and recovering the organic phase, that was extracted 3 times with toluene. The analysis for fatty acids was performed by gas chromatography in a capillary column (Ultra 1.25 m×0.20 mm). The temperature program was 80° C. for 2 minutes, followed by an increase of up to 290° C., at a rate of 10° C./min, up to a total time of 30 minutes.

Example 3: Antimicrobial Test in a Liquid Medium

Antibacterial test: The antimicrobial activity of FLs compounds against different bacterial species of plants and human pathogens was assessed on 96-well microplates. (*Environmental science & technology*, (2009), 43(7), 2498-2504). The FLs were distributed in concentrations comprised between 0.005 and 2 μg/ml in wells, up to a final volume of 200 μl. Next, each well was inoculated with a suspension of the bacterial species corresponding to $10^4$ colony forming units (CFU) per ml, obtained from stationary phased bacteria cultures in a liquid medium for one night (o/n). After 12-24 hours of incubation in a stirrer at 100 rpm at 26° C., it was determined the cell growth of the different bacteria (*Clavibacter michiganensis* subespecie *sepedonicus* C5, *Xanthomonas fragariae*, *Xanthomonas axonospodi* pv. *Citri*, *Pseudomona syringae* pv. *Gladiolos*, *Pseudomona corrugado*, *Erwinia carotovora*, *Rhodococcus fascians*) o 37° C. (*Staphylococcus aureus*, *Staphylococcus epidermidis*, *Enterococcus faecium* CRL35, *Micrococcus* sp., *Bacillus subtilis*, *Listeria monocytogenes*, *Pseudomona aeruginosa*, *Citrobacter* sp., *Escherichia coli* sp., *Salmonella newport* and *Proteus* sp.) by measuring the absorbance at 490 nm in a spectrophotometer for microtitration plates. The $CE_{50}$ value corresponds to an FLs concentration that inhibits 50% of bacterial growth, in comparison with the growth in a medium without FLs. It was used the liquid medium Luria Bertani (LB) (*Molecular cloning: a laboratory manual*, (1989), 2nd ed. Cold Spring Harbor Laboratory Press, Cold Spring Harbor, N.Y) for all of the bacterial strains, with the exception of *Enterococcus faecium* CRL35 and *Listeria monocytogenes* (LPT-Glucose medium, *Journal of AOAC International*, (2014) 97(2), 431-441), *Xanthomonas fragariae* (PS medium, *The Plant Pathology Journal*, (2001), 17(6), 336-341) and *Xanthomonas axonospodi* pv. *Citri* (Cadmus medium, *Canadian journal of microbiology*, (1976) 22(7), 942-948).

Antifungal test: the activity of FLs compounds upon the growth of diverse fungi in microtitration 96 welled plates was assessed (*Applied Microbiology*, (1972) 23(5), 998-1000). The FLs were dispensed in concentrations varying between 0.5 and 100 μg/ml into the wells, that contained a sterile nutritional broth (Potato Dextrose Liquid Medium, *Compendium of methods for the microbiological examination of foods*, (1992), 3rd ed. American Public Health Association, Washington, D.C.) up to a final volume of 200 μl. Each well was inoculated with suspensions of fungus conidia up to a final concentration of $10^4$ CFU/ml. The conidia suspensions were gotten as previously described (*European Journal of Plant Pathology*, (2007) 117, 109-122). After 24-48 hours of incubation in a stirrer (100 rpm) at 28° C., fungal growth was assessed by measuring the absorbance at 490 nm in a spectrophotometer for microtitration plates. The $CE_{50}$ values correspond to an FLs concentration that inhibits 50% of fungal growth, in comparison with the control samples that grow in the same medium without FLs.

Antimicrobial Test on Agar Plates:

The antimicrobial activity of FLs compounds facing diverse plant pathogen species was assessed (*Applied Microbiology*, (1972) 23(5), 998-1000). Different concentrations of FLs (between 5 μg and 100 μg/ml in sterile distilled water) were prepared and a 10 μl drop of each concentration was placed in an LP agar plate until absorption. The soft sterile melted agar (0.7% in water) was cooled down to 40° C. and inoculated with $10^7$ cells/ml of a whole-night culture of strains of plant pathogenic bacteria (*C. michiganensis* subspecies *sepedonicus* C5, *Acidovorax avenae*, *Pseudomonas viridiflava* alb8, *Xanthomonas citri* subsp. *citri*). The corresponding bacterial solution was poured onto LB plates until the agar surface was covered. After a 24 to 48 hour incubation period at 28° C., it was seen a growth inhibition zone around each FLs—containing drop. The minimum inhibitory concentration (MIC) was determined as the lowest concentration of FLs that generated an inhibition of bacterial growth. The LB medium was replaced by Cadmus medium, to assess the inhibition of *Xanthomonas citri* subsp. *citri* growth.

The activity of FLs compounds upon antifungal growth was assessed in like manner to the one described for bacteria. The pure fraction of FLs was diluted in sterile distilled water to provide concentrations comprised between 2 μg/ml and 1000 μg/ml. 50 μl of each concentration were placed on potato-dextrose (PDA) agar plates until their absorption. The soft sterile melted agar (0.7% in water) was cooled down to 40° C. and inoculated with $10^4$ conidia/ml of a whole-night culture of each one of the analyzed plant pathogenic strains (*Corynespora cassiicola*, *Botrytis cinerea* BMM and *Penicillium digitatum* P5). Afterwards, the corresponding conidia solution was poured onto PDA plates up to cover the agar surface. After 48 to 72 hours of incubation period at 28° C., it was seen a growth inhibition zone around each one of the FLs dilutions and the MIC was determined. The MIC was determined three times, at the least, in independent experiments for each plant pathogen.

Example 4

Test for Depolarization of Membranes in *C. michiganensis*

The depolarization of the membrane in the bacterium *C. michiganensis* as controlled through changes in the intensity of the fluorescence emission of the diSC3 (5) membrane-sensitive stain (*Biochemistry*, (1999), 38(22), 7235-7242.). *C. michiganensis* was grown in LB liquid medium and incubated in a stirrer (120 rpm) at 26° C., up to the growth in a median logarithmic phase ($OD_{600}$=0.5). The harvested cells were centrifuged and washed once (glucose 5 mM and HEPES 20 mM pH 7.3) and were suspended again up to a final $OD_{600}$ final=0.05 in the same buffer. 100 µl aliquots were placed in quartz sample cells containing 2 ml of glucose 5 mM, KCl 100 mM and buffer Na HEPES 5 mM, pH 7.2.

After the addition of 0.4 µM de diSC3 (5), the sample cells that contained bacterial cells were incubated at 26° C. until a stable reduction of the fluorescence (about 5 minutes) was reached, what indicated the incorporation of the stain into the bacterial membrane. Afterwards, the FLs, valinomycin or water were added and the stain fluorescence increase at 622 nm (excitation wavelength) and 670 nm (emission wavelength) with a RF-5301 PC spectrofluorometer (Shimadzu, Kyoto, Japan) was recorded. The antibiotic Valinomycin is a $K^+$ selective ionophore that changes the potential of bacterial membranes The addition of valinomycin 1 µM and KCl 100 mM was used as a positive control of a bacterial membrane depolarization. An FLs dose-response test was performed upon the permeability of *C. michiganensis* membrane, through the measurement of the fluorescence after 1 minute for different concentrations (0, 7, 15, 30, 60 and 90 µg/ml) of the FLs fraction.

Example 5: Tests for Protection Against Postharvest Diseases, in Strawberry Fruits The fruits of ripe and healthy strawberries were disinfected by means of a wash with ethanol at 70%, sodium hypochlorite at 10% or with sterile water.

To assess healing effects, the disinfected fruits were inoculated with virulent isolates of *Botrytis cinerea* or *Penicillium digitatum*, applying 20 µl of a suspension of fungus spores ($10^5$ spores/ml) on the surface of each one of the fruits. The infected fruits were incubated at 25° C., 90% of humidity and a 16 hour photoperiod. 3 days after the pathogen inoculation, each fruit was sprayed with FLs at a fungal growth inhibitory concentration (preferably 0.1 mg/ml/). 7 days later the incidence (% of infected fruits) and gravity (degree of surface of an affected fruit) were assessed. As positive controls of the treatment were used the fruits sprayed with a sodium hypochlorite solution at 4% and, as negative controls of growth, the sterile fruits treated with water.

Assessment of preventive effects: the disinfected fruits of strawberry, as was previously described) were sprayed with the FLs compounds at a concentration of, preferably, 0.1 mg/ml and were incubated in a chamber at 25° C., 90% humidity and with a photoperiod of 16 hours. After 2 days of incubation, the surface of the fruits treated with FLs were inoculated with a suspension of 20 µl of fungus spores ($10^5$ spores/ml) of *B. cinerea* or *P. digitatum*, and were incubated in the same culture conditions. 7 days after pathogen inoculation, the incidence (% of infected fruits) and gravity (degree of surface of an affected fruit) were assessed. As positive controls of the treatment were used the fruits sprayed with a sodium hypochlorite solution at 4% and, as negative controls, the sterile fruits treated with water.

Example 6: Tests for Protection Against Postharvest Diseases, in Fruits of Lemon Tree The protective activity of the FLs against pathogens was assessed by treating lemons with an FLs solution 6 hours before (preventive effect) the inoculation of pathogens. The inoculation with lemon pathogens was performed superficially (1 mm in diameter and 2 mm in depth) on the surface of the sprayed fruit, by pricking with a steel scalpel, and then an aliquot of 20 µL of $10^6$ spores/ml of a suspension of a virulent strain of *P. digitatum* was applied.

For the preventive treatments, two FLs concentrations were assessed: 0.1 and 0.2 mg/ml of FLs. As a positive control of the protection against fungal diseases, a commercial fungicide, Imazalil (500 ppm), used in the lemon industry, was utilized, while lemons treated with distilled water were used as negative controls. All of the treated fruits were incubated in growth chambers at 25° C. and 90% of relative humidity. Six days after the pathogen inoculation, an inspection of the fruit was carried out and incidence (number of fruits with symptoms) and infection gravity (fruit surface affected by omycelium development) were assessed. A numerical visual assessment with values ranging from 0 (without mycelium development) to 4 (fruit completely covered in mycelium) was performed From the assessment of the surface affected by the mycelium for each fruit, the gravity index was calculated as the frequency of fruits for each value. The incidence index was defined as the ratio between the quantity of infected lemons (stages 1 to 4), as compared to the total quantity of fruits per treatment.

Example 7: Test for Resistance to Disease, in Strawberry Plants

Healthy plants of the cv"Pajaro" ("Bird") 3 months old of *Fragaria×ananassa* from in vitro tissue cultures, with the FLs compounds at a preferred concentration of 0.03 µg/ml were sprayed and 5 days later they were exposed to the pathogen fungus *Colletotrichum acutatum*, causative agent of the anthracnose disease (*European Journal of Plant Pathology*, (2007) 117, 109-122). The infected plants were incubated in a growth chamber under optimal conditions for the proliferation of the fungi and the development of the disease (28° C., 80% of relative humidity and a photoperiod of 16 hours). Seven days after incubation, the gravity symptoms of petiole disease were assessed according to the scale proposed by Delp and Milholland (*Plant Disease*, (1980), 64(12), 1071-1073), that assigns values of gravity comprised between 1 (healthy plant) and 5 (very grave or dead plant). As positive controls of the induction of a defense against pathogens, the treatment with FLs was replaced by salicylic acid 5 mM or 1 mM of acibenzolar-d-methyl or BTH, a salicylic acid analogous that induces a commercial defense in plants. It is worth noting that the FLs, BTH and salicylic acid concentrations used were subinhibitory for *C. acutatum* growth. As a negative control of defense induction, the plants were sprayed with sterile distilled water.

Example 8: Test of Resistance to Disease in *Arabidopsis* Leaves

*A. thaliana* Col-0 healthy plants 4 weeks old were sprayed with FLs (10 μg/ml) and 4 days later were inoculated with the bacterial pathogen *Pseudomonas viridiflava* alb8 (*Molecular Plant-Microbe Interactions*, (2002), 15(12), 1195-1203.) or the fungal pathogen *B. cinerea* BMM (PLoS Pathogens, (2011), 7(7), e1002148.)

The plants inoculated with *P. viridiflava* were subsequently incubated in culture chambers under controlled conditions (26° C., 80% of relative humidity and 16 hours of photoperiod). Three days after the bacterial inoculation, symptoms of leaf disease were noticed and it was performed a count of viable bacterial cells (CFU), by means of homogeneization of the infected plant tissue, and the cells were seeded in seriated dilutions on plates with LB medium.

Besides, the plants inoculated with *B. cinerea* were incubated in culture chambers at 22° C., 80% of RH in darkness, and three days after the incubation the diameters of leaf lesions were measured. As a positive control for the induction of defenses, it was used a solution of 57 μg/ml of an ellagitannin compound previously described (HeT) isolated from strawberry (*Molecular Plant-Microbe Interactions*, (2012), 25(11), 1430-1439.). As negative controls of defense induction, non-inoculated plants sprayed with distilled water and inoculated plants with infection control were included. The concentrations of FLs and HeT used in the experiment were subinhibitory for pathogen growth, for FLs, for instance, at a concentration comprised between 1 μg/ml and 20 μg/ml.

Example 9: Test for Resistance to Diseases, in Soybean Leaves

Seeds of healthy soybean (*Glycine max*) of the variety elite A8000 RG were made germinate and they grew in greenhouse up to the vegetative stage V3; afterwards, the plants were sprayed with 0.1 mg/ml of FLs compounds and three days later were inoculated with a virulent strain of the pathogen fungus *Corynespora cassiicola*, the causative agent of the ringed spot disease. It should be noted that the FLs concentration utilized in the experiment was subinhibitory for the growth of *C. cassiicola*. As a negative control for defense induction, plants treated with sterile distilled water were used. Besides it was included a treatment with the commercial fungicide Opera (5 ml/L), frequently used in field for the management of the ringed spot. The areas affected in the leaves of the V3 and V4 segments of each pretreated plant were assessed 4, 7 and 10 days after the inoculation, and disease severity was expressed as the area under the disease progress curve (AUDPC) after Shaner and Finney (*Phytopathology*, (1977), 67(8), 1051-1056).

Example 10: Test for Resistance to Diseases, in Strawberry Fruits

Fruits inoculated under controlled conditions of growth: Healthy and ripe strawberries collected in the field were disinfected by means of washing in ethanol at 70%, sodium hypochlorite at 10% and sterile water. The disinfected fruits were immersed in an FLs solution (10 μg/ml) and incubated at 25° C., 90% of humidity and 16 hours of photoperiod. After 2 days of incubation, the surface of the treated fruits was inoculated with a fungus spore suspension of 20 μl ($10^5$ spores/ml) of *B. cinerea* or *P. digitatum*, and were incubated in the same growth conditions above described. Seven days after the pathogen inoculation, the incidence (% of infected fruits) and the severity (degree of affected fruit surface) of the disease were assessed. The fruits sprayed with a solution of sodium hypochlorite at 4% were used as a protection positive control and the sterile fruits treated with water, as negative controls. Besides, a treatment with the plant defense inducer HeT (0.8 mg/ml) was included. The FL and HeT concentrations were subinhibitory for fungal growth.

Fruits under pressure of a natural inoculum: The induction of plant defenses was determined using subinhibitory FLs (10 μg/ml) or HeT (0.8 mg/ml) concentrations for fungal growth. Strawberry plants grown in field received 2 applications of the tested products, the first one when 80% of the plants was blooming and the second application, 15 days later. The degree of protection afforded by each treatment was measured as harvested fruits incubated in a growth chamber at 25° C., 90% of humidity and 16 hours of photoperiod. The fruits were assessed 5 days after harvest and the severity of the disease (degree of affected fruit surface) was analyzed, and they were compared to untreated fruits (negative control) and fruits treated with the commercial biological fungicide Gluticid (3 mg/ml) (positive control for protection). The experiment was carried out using a randomized complete block design, that has 5 blocks of 30 plants for each treatment. The plants were under a conventional cultivation management between August and September 2009 in the locality of Mercedes, Tucuman province.

Example 11: Production of Reactive Oxygen Species (ROS) in *A. thaliana* Leaves The in situ detection of the production of superoxide radicals in *A. thaliana* leaves was carried out through NBT histochemical staining, according to Wohlgemuth et al. (*Plant Cell Environ.*, (2002), 25 717-726.), with minor modifications. The plants were subjected to treatments with FLs (10 μg/ml) or treatments with water (negative control) by means of leaf spraying. 0, 2, 4 and 6 hours after the treatment the leaves were removed from the treated plants and immersed in potassium phosphate buffer 50 mM (pH 7.8) that had 0.1% of NBT and 10 mM of sodium azide. The leaves were stained by infiltrating them in vacuum conditions, by means of a double vacuum shock treatment for 1 minute and 100 mm of Hg, and afterwards they were incubated for 1 hour in darkness (without vacuum). After incubation in darkness, the leaves were first immersed in ethanol at 96% (v/v) to remove the remaining chlorophyll and then were clarified and preserved in lactic acid/glycerol/water (3:3:4 v/v/v). The production of superoxide was visualized as purple formazan deposits within leaf tissues.

Example 12: Accumulation of Callose in *A. thaliana* Leaves

Callose deposits were visualized using the method described in (*Protoplasma*, (1956), 45(4), 552-559). The leaves of pretreated *A. thaliana* plants were discolored in ethanol at 96% and gradually rehydrated by immersing them sequentially in ethanol at 50%, ethanol at 25% and finally in $K_2HPO_4$ 67 mM (pH 12). After the rehydration, the leaves were stained for 1 hour with aniline blue at 0.05% in darkness and were finally immersed in glycerol at 30%, before being analyzed under UV light in a fluorescence microscope, that visualizes an accumulation of callose as bright blue spots. The pretreatments of *A. thaliana* plants consisted of spraying with 10 μg/ml of FLs or 0.0857 mg/ml of HeT (positive control) or distilled water (negative control), and 6 days after the treatment, the detached leaves were stained the way that was previously described. Besides, some plants were inoculated with the virulent pathogen *Pseudomonas viridiflava* alb8 4 days after the treatment with FLs or water and stained with aniline blue 2 days postinoculation.

Example 13: Induction of the Genetic Expression in *A. thaliana*

The assessment of the genetic expression in *A. thaliana* plants was performed by means of real time PCR (qPCR). The total RNA was purified from leaves of *A. thaliana* plants 0, 1, 3, 6 and 24 hours after the leaf spraying with LFs 10 μg/ml or distilled water (negative control). The treated leaves were detached from their plants and placed in a mortar, frozen in liquid nitrogen and homogeneized with a pestle. Total RNA was extracted following the Trizol method according to Chomczynski and Sacchi (Anal. Biochem. (1987), 162, 156-159). Briefly: 150 mg of leaves were homogeneized in 1 ml of Trizol reactive, purified in a mixture of chloroform: isoamyl alcohol and finally treated with DNAse I. The purity and the quality of the extracted RNA were determined by means of spectrophotometry and electrophoresis, respectively. The retrotranscription was performed with the M-MLV enzyme of reverse transcriptase (Thermo Scientific) following the manufacturer's instructions. The resulting cDNA was analyzed by means of real time PCR using iQ SYBR Green Supermix (BioRad). It was studied the expression of the PRI genes (At2g14610; forward primer: GTCTCCGCCGTGAACATGT (SEQ ID No 1); reverse primer: CGTGTTCGCAGCGTAGTTGT) (SEQ ID No 2) y PDF1.2 (At5g44420; forward primer: TTTGCTTCCATCATCACCCTTA (SEQ ID No 3); reverse primer: GCGTCGAAAGCAGCAAAGA) (SEQ ID No 4). The constitutive expression gene EF1 (At1g18070, forward primer: AGCACGCTCTTCTTGCTTTC (SEQ ID No 5), reverse primer: GGGTTGTATCCGACCTTCTTC) (SEQ ID No 6) was used as load control for all of the samples.

Example 14: Studies on Growth Promotion in *A. thaliana*

Plants of *A. thaliana* Col-0 and the transgenic line DR5::GUS were cultured using a culture system in agar plate vertically oriented, to assess above ground growth and root development (*The Plant Cell*, (2007), 19(3), 831-846.). The pure FLs fraction (0.16 μg/ml) was added to the melted MS medium (50° C.), that was subsequently poured in Petri plates. The phenotypes were observed 7, 10 and 14 days after seed germination. By way of comparison, the effects of auxins upon the growth and development of plants cultured in MS medium supplemented with 5 ng/ml of naphthalene acetic acid (NAA) were assessed. The transgenic plants DR5::GUS carry a synthetic promoter (DR5) strongly sensitive to auxins, that directs and regulates the expression of the reporter gene of the β-glucuronidase (gusA), that may be used to detect auxin distribution and plant tissue responses, by means of histochemical staining (*Plant Physiology*, (2002), 130(1), 199-209). To visualize the expression of gusA in different plant tissues, the seedlings were made to grow as previously shown, were collected and immersed in the chromogenic substrate 5-bromo-4-cyloro-3-indolil glucuronide (X-Gluc) for 10 minutes. Afterwards they were incubated at 37° C. in darkness for 16 hours. After the incubation in darkness, the seedlings were rinsed first with a sodium phosphate buffer 50 mM, pH 7; then they were discolored with ethanol at 95% (v/v) and finally were immersed in ethanol at 70%/v/v). Images of *A. thaliana* tissue stained with X-Gluc were recorded using an optical microscope with a 10× magnification and furnished with a digital camera. The experiments were repeated three times using 10 samples of plants/experiment.

It was assessed the growth promotion in *A. thaliana* Col-0 plants cultivated in greenhouse (25° C., 16 hours of photoperiod and 70% of RH) sprayed with FLs (1.6 μg/ml) in the above ground parts of healthy plants 3 weeks old, in the initial stages of blooming (beginning of the inflorescence) and it was assessed the quantity of total siliques per plant in week 5 after treatment. The plants sprayed with distilled water were used as control treatment. The experimental design consisted of 4 random blocks of 6 plants per block for each treatment.

Example 15: Strawberry Throughput in Field Conditions

The effects of growth promotion upon strawberry plants (*Fragaria×ananassa* cv Camarosa) were assessed by spraying the leaves with FLs (50 μg/ml) or deionized water (negative control) together with a silicone based adjuvant, ethoxilated nonylphenol (0.03%). It was used a field test with a design of randomized blocks containing 5 blocks of 30 plants, under conventional management for both treatments between June and November, during two growth seasons (2010 and 2012) at the Mercedes locality, Tucuman province. All of the plants received a monthly application of FLs or water, from June to October and every two weeks. Ripe fruits were harvested and it was determined the total weight of fruit and the commercial fruits for each block, on a monthly basis. Subsequently, a statistical analysis was performed, that would express the weight of a fruit per plant for the assessed month. It was defined as commercial fruit the fruits having a weight greater than 10 g, or even above that; 80% of ripening, or even more, with no signs or symptoms of disease or mechanical damage.

Example 16: Greenhouse Test in the Configuration of the Soybean Pod

The soybean plants (A8000 RG, ripening group VIII), sowed in pots with a low fertility sterile substrate and cultivated under greenhouse controlled conditions, were treated by spraying the above ground parts with FLs (50 μg/ml) or water (negative control), together with a silicone based adjuvant, ethoxilated nonylphenol (0.3%), in the growth stages V1, V7, R1 and R3. As a positive control of growth promotion, the seeds of soybean were treated with the commercial bioinoculant BIAGRO10 (BIAGRO S.A., Las Heras, Argentina), based on E109 bacterial strains of *Bradyrhizobium japonicum*, following the manufacturer's instructions (77 g/L for 190 kg of seeds). The test was carried out in a greenhouse with temperatures that varied between 25 and 30° C., and an 18-hour controlled photoperiod (12000-18000 lux). For each treatment, 4 blocks of 4 plants each were used. Once the plants had reached the R8 stage, the total quantity of pods per plant for each treatment was determined.

Example 17: Growth Promotion in Sugar Cane Plants Cultivated in a Greenhouse Sugar cane plants (*Saccharum* spp. hybrid var. LCP 85-384) were obtained from uninodal stakes planted in pots (4 liter volume) with a sterile substrate. The plants were treated twice with FLs (14 μg/ml) or water (negative control), first by immersion of each stake for 1 hour before being planted and, secondly, by leaf spraying 2 months after the planting. All of the treatments were applied together with a silicone based at (0.03%) adjuvant, ethoxylated nonylphenol. The control treatment of positive growth promotion was performed using the commercial bioinoculant Gramen *Caña* (Azur Agro Business, La Plata, Argentina), based on bacterial strains of the genus *Azospirillum*, and it was carried out through the immersion of uninodal stakes according to the manufacturer's specifications.

The experiment was carried out in a greenhouse with temperatures ranging from 28° C. to 35° C. and an 18 hours of light-controlled photoperiod. For each treatment, 5 blocks of 5 plants each were used. Four months later, the weight of fresh root, the ratio between the above-ground part fresh weight and the stem length per plant were calculated for each treatment.

Example 18 Method for the Extraction and Obtention of FLs Compounds

The FLs compounds were obtained from different tissues of crop species of the genuses *Fragaria, Duchesnea, Potentilla* and other genuses pertaining to the Rosaceae family. The extraction of FLs was carried out in an aqueous medium acidified with trifluoroacetic acid (TFA), homogenizing the plant material (0.1 g of fresh weight//ml of solvent) and stirring at 20 rpm (4° C.) for 2 hours. After centrifugation, the clarified extract was recovered at 10,000×g, 15 min. and was divided into fractions by preparative chromatography, a solid phase extraction cartridge (SPE) that contained 10 g of C18-E matrix (Phenomenex, EE. UU.) being used. 20 ml of clarified extract were loaded into the column and afterwards a washing with 80 ml of TFA at 0.1% diluted in water was performed. The initial volume load, together with the washing flow were collected as a preliminary purification stage, because the column molecule does not absorb FLs molecules.

The fraction recovered (about 80 ml) was concentrated 40 times (2 ml) in a vacuum concentrator (SpeedVac, Thermo Scientific) and was additionally purified by means of HPLC using a reversed phase chromatography column (SOURCE 5RPC, GE Healthcare Biosciences AB). Once again, as in the case of the SPE column, the FLs do not interact with the reversed phase matrix and so they pass through the column, together with the TFA 0.1% diluted in water. The flow fraction collected (2 ml) was concentrated in vacuum conditions up to dryness.

The dry concentrate from the reversed phase column was dissolved in 1 ml of water and was applied to an HPLZ Zorbax-Amino (Waters, EE.UU.) normal phase column. The elution of the united material was performed using an isocratic gradient with 80% of acetonitrile and a flow of 1 ml/min. The desired fraction was collected after 5 minutes approximately, concentrated under vacuum up to dryness and resuspended in 1 ml of water. In a final purification stage, it was used a high-performance anion exchange chromatography system with an amperometric detector (HPAEC-PAC) with a Carbopac PA-1 column (4×250 mm, Dionex, EE. UU.) and the FLs were eluted by means of a gradient of a tripartite solvent (200 NaOH mM as solvent A, water as solvent B and AcONa 1M as solvent C). An initial solvent gradient of 25% A, 75% B and 0% C was kept for 10 minutes, followed by a linear gradient that changes the concentrations of solvents B and C up to reaching, after 30 minutes, a final solution that contains 25% A, 25% B and 50% C. The flow rate was 1 ml per minute and the pure FLs were recovered 6.49 minutes later.

Example 19 Production of the Composition According to the Present Invention

The addition of ethanol 96° up to a 2% concentration enables the FLs preservation for 6 months without modifications at room temperature, and for 2 years refrigerated to 4° C.

The product obtained (FLs) is completely water miscible and compatible with agricultural adjuvants. FLs compositions may be made with nonylphrenol ethoxylates at 0.03% or FLs compositions with commercial methylated vegetable oils at 0.15%.

Example 20: Obtention Method of an FLs Enriched Extract

Leaves of a strawberry commercial cultivation were dried to remove water from plant tissues, up to reaching the 25% of the initial weight: this allows for the preservation of the leaves from 2 to 5 years at room temperature in a dry environment. The drying was performed by evaporation on grids in a greenhouse and favoring their aeration during 7 to 10 days.

Afterwards the dried leaves were ground using a knife mill that allows for the obtention of 3 mm particles Then the extraction was performed through the maceration of the ground dried leaves in an adequate solvent to extract and solubilize the FLs: for instance, as a solvent was used 0.5% of concentrated 10× lemon juice in deionized water, in a proportion of 0.25 g of dried ground leaves in 1 ml of solvent. It was incubated 24 hs utilizing a paddle—type stirrer at low revolutions (5-10 rotations/min).

Next, it was performed a reextraction of FLs present in the remaining plant material, by adding 2 volumes of ethanol 96° for each extract volume, and the reextraction was incubated for 2 hours at room temperature.

A filtration was carried out to separate the extract from the solid plant material, using a cloth bag vacuum-forced (300 mm Hg) filter with a reusable cloth. An ulterior precipitation stage allowed for the insolubilization of sugars and other compounds without activity. To do this an incubation was made of the extract filtered statically for 24 hours at room temperature. A new filtration of the extract was performed with a cloth bag vacuum-forced (300 mm Hg) filter with a reusable cloth.

Then the extract was concentrated to completely remove the ethanol and part of the water content. To do that, a vacuum distillation in a simple distillation apparatus with adjustable temperature and pressure was performed. The extract thus obtained has, approximately, 0.1 mg/ml of FLs.

The addition of ethanol 96° up to a concentration of 2% allows for the preservation of the product for 6 months at room temperature without modifications, and for 2 years refrigerated down to 4° C.

The product obtained is completely water miscible and compatible with agricultural adjuvants such as nonylphrenol ethoxylates (at 0.03%) and commercial methylated vegetable oils (at 0.15%).

What is claimed is:

1. A composition for the promotion of plant growth comprising a fatty acid glycoside having the general formula:

GalNAc-GalNAc-Glc-O—R, where GalNAc is α- or β-D-N-acetylgalactosamine, Glc-O—R is a molecule of α- or β-D-glucose esterified to a monounsaturated fatty acid (R), where R is selected from 12:1(n) and where n is an integer between 2 and 11; 11:1(n) and where n is an integer between 2 and 10; 10:1(n), and where n is an integer between 2 and 9; 9:1(n), and where n is an integer between 2 and 8; 8:1(n), and where n is an integer between 2 and 8; 7:1(n) and where n is an integer between 2 and 7; and 6:1(n), and where n is an integer between 2 and 6; and an adjuvant selected from the group consisting of nonylphenol ethoxylate and methylated vegetable oils.

2. The composition according to claim 1, wherein the plants are selected from the group consisting of soybean, strawberry, lemon tree, sugar cane and *A. thaliana*.

3. A composition for the promotion of plant growth comprising a fatty acid glycoside having the general formula:

GalNAc-GalNAc-Glc-O—R, where GalNAc is α- or β-D-N-acetylgalactosamine, Glc-O—R is a molecule of α- or β-D-glucose esterified to a monounsaturated fatty acid (R), where R is selected from 12:1(n) and where n is an integer between 2 and 11; 11:1(n) and where n is an integer between 2 and 10; 10:1(n), and where n is an integer between 2 and 9; 9:1(n), and where n is an integer between 2 and 8; 8:1(n), and where n is an integer between 2 and 8; 7:1(n) and where n is an integer between 2 and 7; and 6:1(n), and where n is an integer between 2 and 6; and an adjuvant;

wherein the composition comprises a concentration ranging from 0.16 µg/ml to 50 µg/ml of the fatty acid glycoside and a concentration ranging from 0.013% and 0.07% of the nonylphenol ethoxylates compound.

4. A composition for the promotion of plant growth comprising a fatty acid glycoside having the general formula:

GalNAc-GalNAc-Glc-O—R, where GalNAc is α- or β-D-N-acetylgalactosamine, Glc-O—R is a molecule of α- or β-D-glucose esterified to a monounsaturated fatty acid (R), where R is selected from 12:1(n) and where n is an integer between 2 and 11; 11:1(n) and where n is an integer between 2 and 10; 10:1(n), and where n is an integer between 2 and 9; 9:1(n), and where n is an integer between 2 and 8; 8:1(n), and where n is an integer between 2 and 8; 7:1(n) and where n is an integer between 2 and 7; and 6:1(n), and where n is an integer between 2 and 6; and an adjuvant;

wherein the composition comprises a concentration ranging from 0.16 µg/ml to 50 µg/ml of the fatty acid glycoside and a concentration ranging from 0.15% to 1.16% of methylated vegetable oils.

* * * * *

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: At2g14610 forward primer

<400> SEQUENCE: 1
gtctccgccg tgaacatgt                                                  19

<210> SEQ ID NO 2
<211> LENGTH: 20
<212> TYPE: DNA
<213> ORGANISM: Artificial Sequence
<220> FEATURE:
<223> OTHER INFORMATION: At2g14610 reverse primer

<400> SEQUENCE: 2
cgtgttcgca gcgtagttgt                                                 20

<210> SEQ ID NO 3
<211> LENGTH: 22
<212> TYPE: DNA
<213> ORGANISM: Artificial Sequence
<220> FEATURE:
<223> OTHER INFORMATION: At5g44420 forward prime

<400> SEQUENCE: 3
tttgcttcca tcatcaccct ta                                              22

<210> SEQ ID NO 4
<211> LENGTH: 19
<212> TYPE: DNA
<213> ORGANISM: Artificial Sequence
<220> FEATURE:
<223> OTHER INFORMATION: At5g44420 reverse primer

<400> SEQUENCE: 4
gcgtcgaaag cagcaaaga                                                  19

<210> SEQ ID NO 5
<211> LENGTH: 20
<212> TYPE: DNA
<213> ORGANISM: Artificial Sequence
<220> FEATURE:
<223> OTHER INFORMATION: At1g18070 forward primer

<400> SEQUENCE: 5
agcacgctct tcttgctttc                                                 20

<210> SEQ ID NO 6
<211> LENGTH: 21
<212> TYPE: DNA
<213> ORGANISM: Artificial Sequence
<220> FEATURE:
<223> OTHER INFORMATION: At1g18070 reverse primer

<400> SEQUENCE: 6
gggttgtatc cgaccttctt c                                               21